United States Patent
Stewart

(10) Patent No.: US 9,721,416 B2
(45) Date of Patent: Aug. 1, 2017

(54) AUTHENTICATION APPARATUS AND METHOD

(71) Applicant: INNOVIA FILMS LIMITED, Wigton, Cumbria (GB)

(72) Inventor: Robert Laird Stewart, Wigton (GB)

(73) Assignee: INNOVIA FILMS LIMITED, Wigton, Cumbria (GB)

( * ) Notice: Subject to any disclaimer, the term of this patent is extended or adjusted under 35 U.S.C. 154(b) by 0 days.

(21) Appl. No.: 14/888,914

(22) PCT Filed: Apr. 30, 2014

(86) PCT No.: PCT/GB2014/051338
§ 371 (c)(1),
(2) Date: Nov. 3, 2015

(87) PCT Pub. No.: WO2014/181086
PCT Pub. Date: Nov. 13, 2014

(65) Prior Publication Data
US 2016/0086411 A1 Mar. 24, 2016

(30) Foreign Application Priority Data

May 10, 2013 (GB) .................................. 1308434.8

(51) Int. Cl.
*G06K 9/74* (2006.01)
*G07D 7/12* (2016.01)
(Continued)

(52) U.S. Cl.
CPC ............. *G07D 7/124* (2013.01); *G01N 21/21* (2013.01); *G01N 21/59* (2013.01); *G02B 5/3083* (2013.01);
(Continued)

(58) Field of Classification Search
CPC ........ G02B 5/285; G02B 5/201; G02B 5/305; G02B 27/28; G02B 5/0816; G02B 5/0841;
(Continued)

(56) References Cited

U.S. PATENT DOCUMENTS

2012/0314207 A1* 12/2012 Bain .................... G01B 11/06
356/73
2015/0279142 A1* 10/2015 Stewart ................... G06K 7/00
194/207

FOREIGN PATENT DOCUMENTS

WO      2006/047422      5/2006
WO      2009/133390      11/2009
(Continued)

OTHER PUBLICATIONS

International Search Report of International Application No. PCT/GB2014/051338 mailed Apr. 30, 2014.

*Primary Examiner* — Michael P Stafira
(74) *Attorney, Agent, or Firm* — Ping Wang; Andrews Kurth Kenyon LLP

(57) ABSTRACT

The present invention provides an authentication apparatus operative to determine the authenticity of a polymer film, comprising an optically-based birefringence measuring arrangement operative to measure a first effect influenced by a birefringence characteristic of said film from a first angle comprising a non-normal angle to a plane of said film, and at least one of: a second angle; and a third angle; and wherein said apparatus is operative to: compare a value, or range of values, representative of said first effect as measured from said first angle with a value, or range of values representative of a specified first effect corresponding to a predetermined birefringence characteristic of an authentic polymer film for said first angle; compare a value, or range of values, representative of said first effect as measured from (Continued)

said at least one of said second and third angles with a value, or range of values representative of a specified first effect corresponding to a predetermined birefringence characteristic of an authentic polymer film for respective second and/or third angles; and output an authenticity signal indicative of authenticity or otherwise of said film based upon said comparisons. There are also provided one or more methods of determining the authenticity of a polymer film.

15 Claims, 19 Drawing Sheets

(51) Int. Cl.
G06K 9/00 (2006.01)
G07D 7/20 (2016.01)
G01N 21/21 (2006.01)
G01N 21/59 (2006.01)
G02B 5/30 (2006.01)

(52) U.S. Cl.
CPC ........... *G06K 9/00046* (2013.01); *G07D 7/12* (2013.01); *G07D 7/122* (2013.01); *G07D 7/20* (2013.01)

(58) Field of Classification Search
CPC .... G02B 5/30; G02B 5/3041; G02B 27/2214; G02B 5/223; G02B 5/32; G02B 6/0068; G02B 6/0076; G02B 1/08
See application file for complete search history.

(56) References Cited

FOREIGN PATENT DOCUMENTS

| WO | 2010/001165 | 1/2010 |
| WO | 2012/020263 | 2/2012 |
| WO | 2012/032361 | 3/2012 |

* cited by examiner

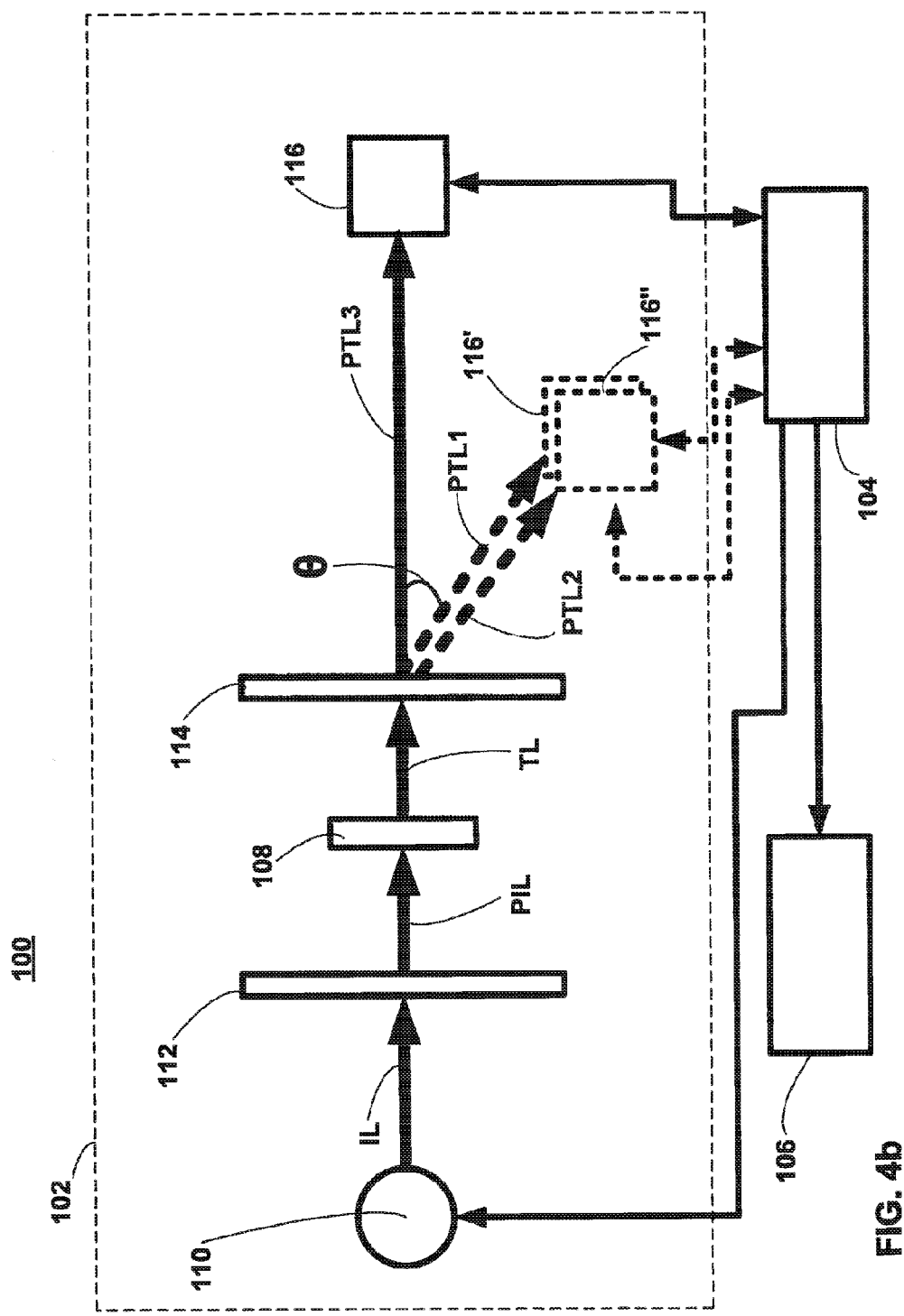

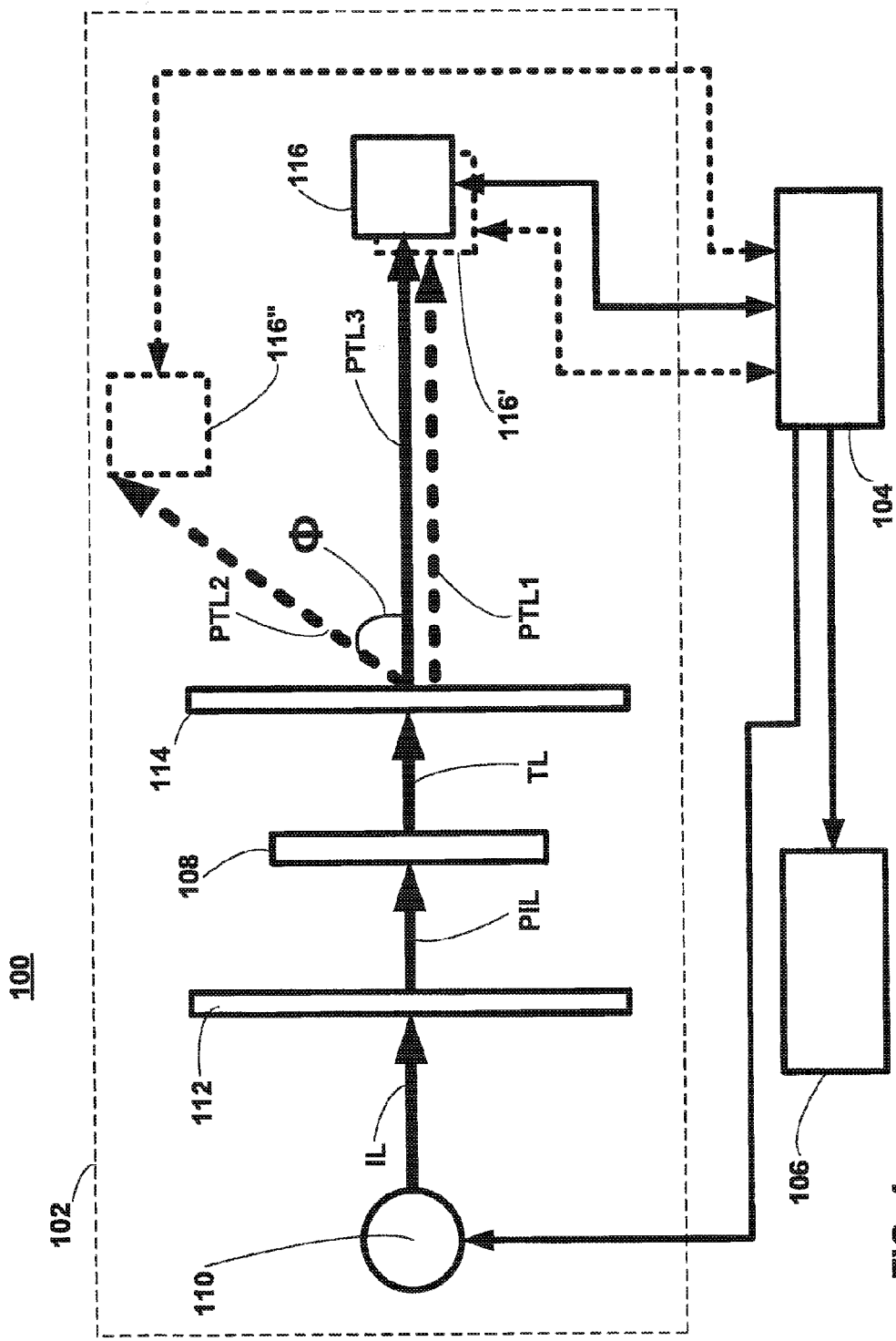

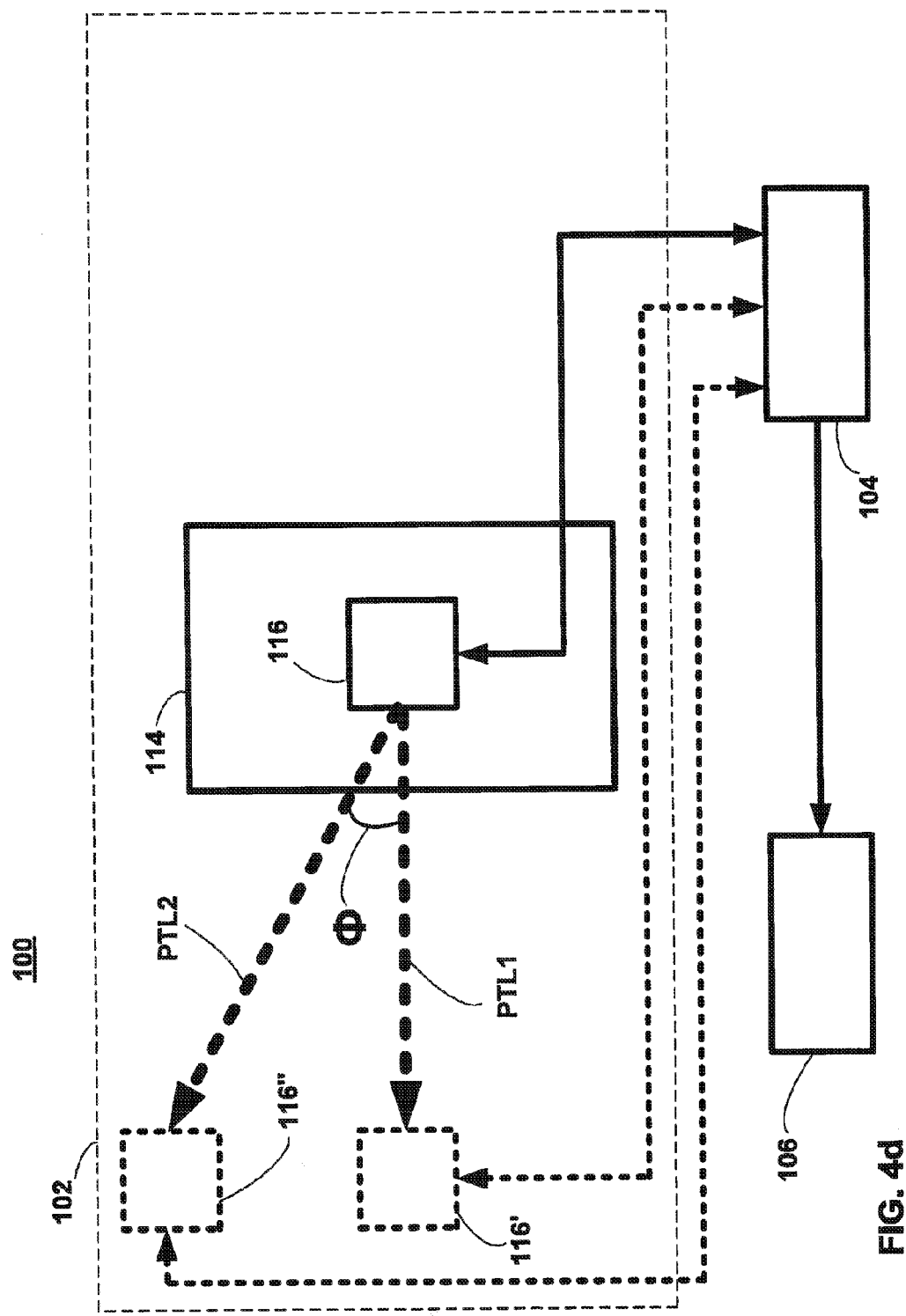

AUTHENTICATION APPARATUS AND METHOD

This application is a national stage application of International Patent Application No. PCT/GB2014/051338, filed Apr. 30, 2014, which claims priority to United Kingdom patent Application No. 1308434.8, filed May 10, 2013. The entirety of the aforementioned applications is incorporated herein by reference.

FIELD

The present invention relates to an authentication apparatus and method, and particularly, but not exclusively, to an authentication apparatus for and method of authenticating a polymer film.

BRIEF DESCRIPTION OF THE DRAWINGS

One or more specific embodiments in accordance with aspects of the present invention will be described, by way of example only, and with reference to the following drawings.

FIGS. 4a to 4d schematically illustrate perspective, top-plan, side and end views of an authentication apparatus in accordance with one or more embodiments of the present invention;

DETAILED DISCRETION

Figure 1:
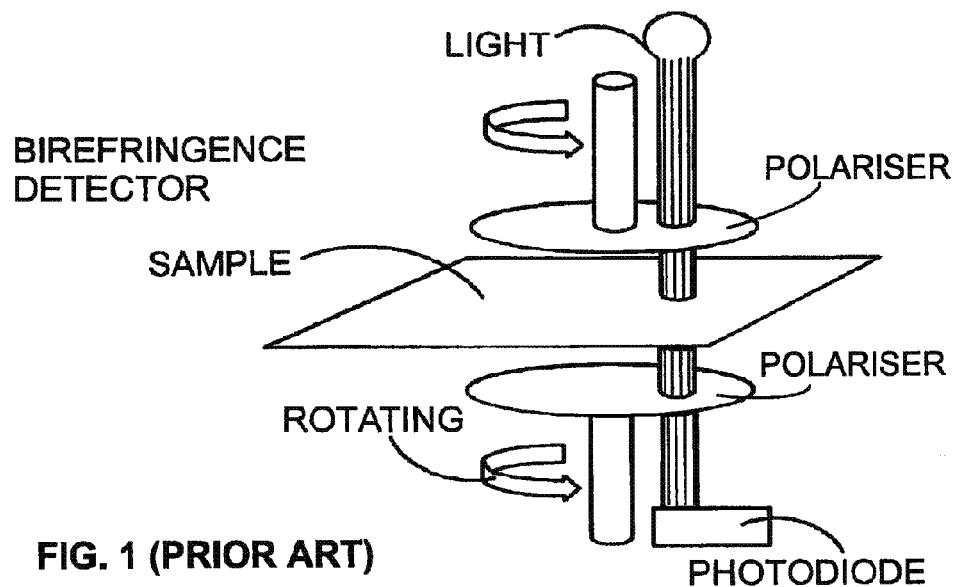
FIGS. 1 to 3 schematically illustrate components of known apparatus for implementing different methods of observing birefringence.

Polymer films are increasingly being used as substrates in fields where security, authentication, identification and anti-counterfeiting are important. Polymer-based products in such areas include for example bank notes, important documents (e.g. ID materials such as for example passports and land title, share and educational certificates), films for packaging high-value goods for anti-counterfeiting purposes, and security cards.

Polymer-based secure materials have advantages in terms of security, functionality, durability, cost-effectiveness, cleanliness, processability and environmental considerations. Perhaps the most notable amongst these is the security advantage. Paper-based bank notes, for example, can be relatively easy to copy, and there is lower occurrence of counterfeits in countries with polymer-based bank notes compared to paper-based bank notes. Polymer-based bank notes are also longer-lasting and less-easily torn.

Security materials based on polymer films are amenable to the incorporation of a variety of visible and hidden security features. Since the introduction of the first polymer bank notes approximately 30 years ago, security features have included optically variable devices (OVD), opacification features, printed security features security threads, embossings, transparent windows and diffraction gratings. Aside from complicated security features there is also the more immediate advantage that the high temperatures used in copying machines will often cause melting or distortion of polymer base-material if counterfeiters attempt simply to copy secure materials (e.g. bank notes) using such machines.

A variety of polymers may be used as secure substrates. Amongst these is polypropylene film. The three main methods of manufacturing polypropylene film are the stenter method, the cast method and the bubble method.

In the cast and stenter methods, polymer chips are typically placed in an extruder and heated so that an extrudate is forced out of a slit die onto a chilled roller to form a film (in the case of the cast method) or a thick polymer ribbon (in the case of the stenter method). In the stenter method, the thick polymer ribbon is then reheated and then stretched lengthways (termed the "machine direction") and widthways (termed the "transverse direction") to form a film. In general, the stretching in the machine and transverse directions occurs sequentially and is generally non-homogenous, i.e. there is a greater degree of stretching in the transverse direction compared with the machine direction.

In the bubble method, the polymer is extruded not through a slit die but through an annular die, to form a relatively thick extrudate, in the form of a hollow cylinder or "drainpipe" shape through which air is blown. The annular die is at the top of an apparatus which is typically the equivalent of several storeys high (for example 40 to 50 meters). The extrudate moves downwards and is heated sequentially so that it is expanded to form a bubble. The bubble is then slit into two half-bubbles, each of which may be used individually as "monoweb" films; or alternatively the two halves may be nipped and laminated together to form a double thickness film (or the bubble may be collapsed to form a double thickness film). Typically there are three concentric annuli at the die, so that the hollow cylinder is an extrudate of three layers. For example, there may be a core layer of polypropylene with a terpolymer skin layer on one side and another terpolymer skin layer on the other side. In this case the monoweb would consist of three layers with polypropylene in the middle and the double web would consist of five layers because the layer in the middle would be the same skin layer (terpolymer) of each half-bubble. Many other possible arrangements and components are possible, for example in terms of the number of annuli, type of skin layer, type of core layer, etc.

Thus the bubble method results in a thin film (for example 10 to 100 microns thick) by forming a bubble whereas the stenter method results in a thin film by stretching the material on a flat frame. In the bubble method, stretching occurs simultaneously in both the machine and transverse directions, and the degree of stretching in both directions is generally the same. Thus, the bubble method results in a homogeneously stretched film which is different to and for some purposes advantageous over stenter film. Biaxially Oriented Polypropylene (BOPP) film is made by the bubble process by Innovia Films Ltd., Wigton, UK. In addition to polypropylene, other polymers (e.g. LLDPE, polypropylene/butylene copolymers) may also be formed as thin films using the bubble process.

It is known to introduce features in a film used as a substrate for security documents, identity documents or value documents and articles which are not readily apparent to a potential unauthorised user or counterfeiter, and which even if identified cannot be readily reproduced. The introduction of such security features may also be applicable to other tokens or articles requiring verification of authentication, such as entrance documents and tickets.

Previous authentication apparatus and methods make use of known sheets of security document substrate which are permeable to electromagnetic radiation, for example, transparent in the visible region of the electromagnetic spectrum. It is known to create security documents, such as banknotes, by printing opaque inks onto sheets of transparent plastics substrate material, leaving a transparent window. The resulting window provides an overt security feature which is conspicuous to the human eye. It is known to print, etch or embed additional optical security features, such as optically variable devices formed by diffraction gratings, onto or into the resulting transparent windows, to provide additional overt security features. It is known to provide automatic authentication apparatus which can determine authenticity from the presence or absence of these additional optical security features, but such apparatus is typically complex and expensive.

Figure 2:
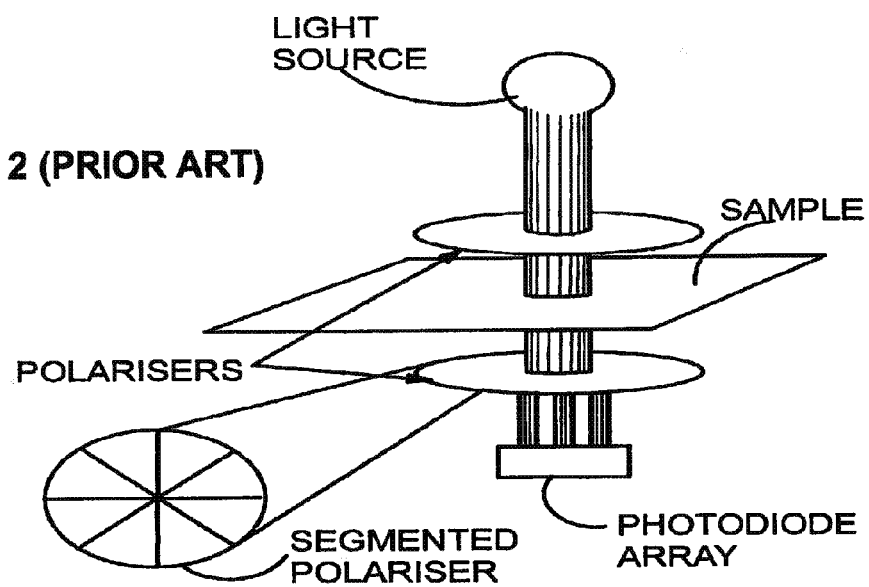
Figure 3:
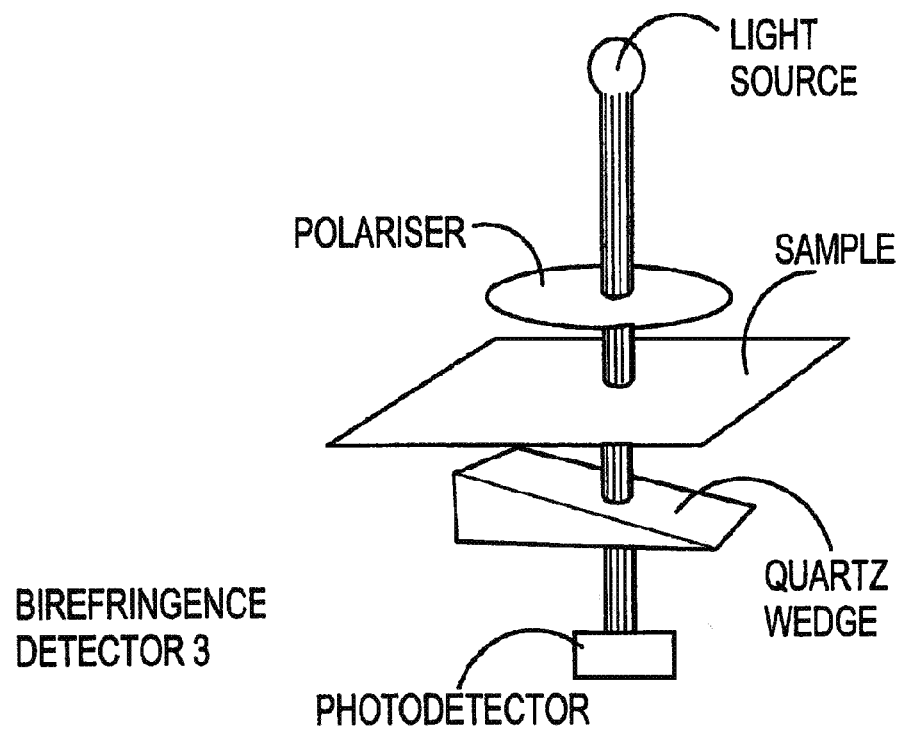
Figure 4A:
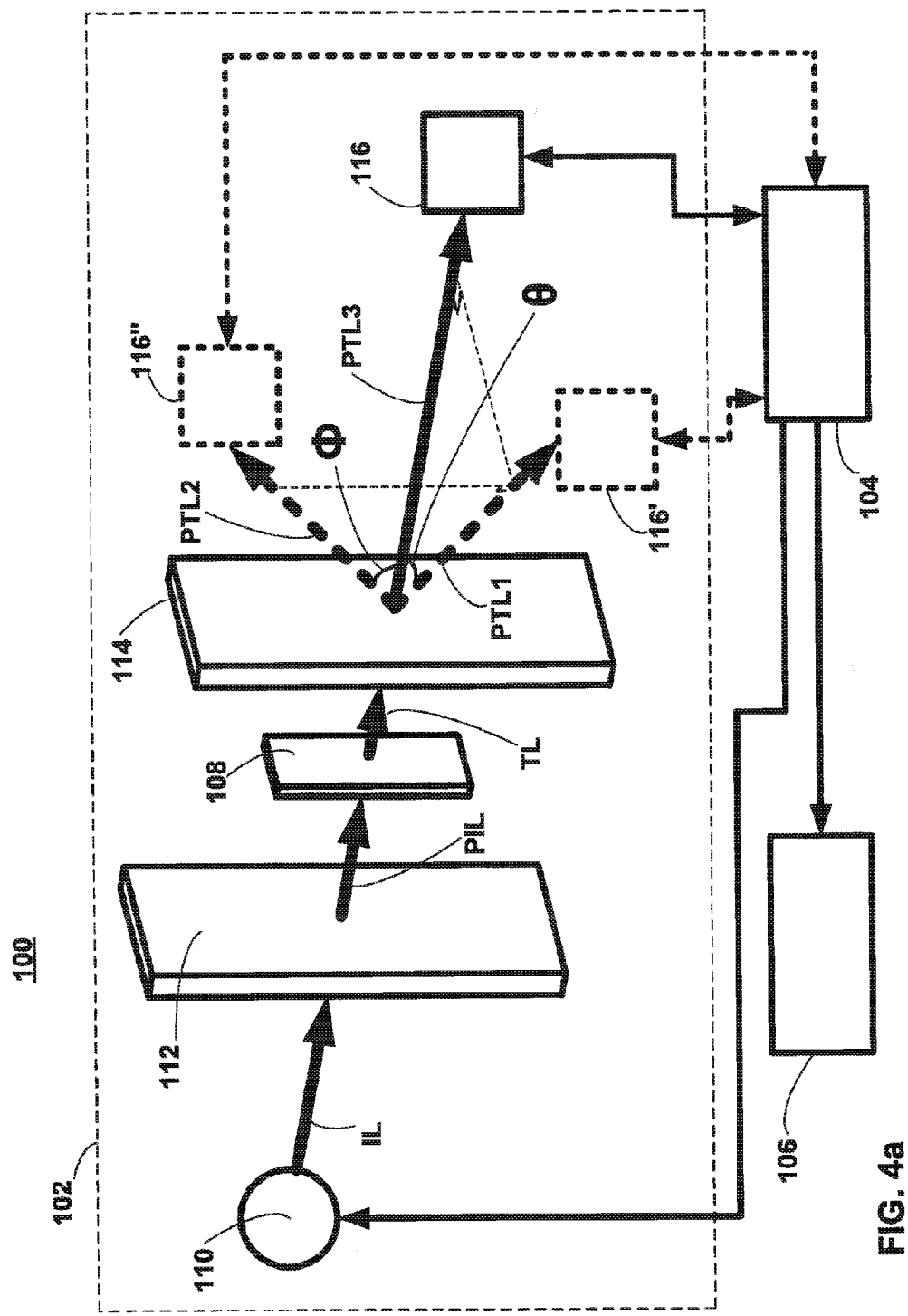

WO 2009/133390 discloses a method of authenticating a polymer film comprising measuring the birefringence of a core layer therein. FIGS. 1 to 3 show components of apparatus for different methods of observing birefringence as disclosed in WO 2009/133390.

Birefringence, or double refraction, is a property of materials caused by differences in the refractive indices of the material for the two different polarisations, s- and p-, and between the two axes of its surface plane.

A birefringent material, when presented with polarised light (e.g. formed from light passed through a first polariser), splits the light into ordinary, O- and extraordinary, E-rays which are both retarded by transmission through the birefringent material, but to different degrees. After transmission through a second polariser at 90° with respect to the polarised light (e.g. at 90° to the polarisation orientation of the first polariser), the two rays (i.e. ordinary and extraordinary) recombine and interfere with one another destructively or constructively. The effect generated is of variable transmission in the form of a sine wave as the birefringent material is rotated from the minima (0° with respect to the polarisers) to the maxima (45° with respect to the polarisers). This happens because at 0° and 90°, the birefringent material simply does the same as those polarisers it is in-line with, whereas at 45°, a second polarisation event occurs. Light passing through the first polariser is exactly 45° rotated from the E-plane and the O-plane of the birefringent material; in consequence, the birefringent material splits this light up into an O-ray and an E-ray that are 45° rotated from the incident polarised light. Upon reaching the second polariser (itself now 45° rotated from the new O-ray and E-ray), the two rays combine in order to pass through the second polariser.

Polarised light is capable of effectively rotating through 90° if assisted by an initial forced partial rotation step. If the birefringent material is rotated at other angles, then this will affect the portion of the polarised light that can become an O-ray or E-ray in the birefringent material and will thus also affect the portion of light that is ultimately transmitted by the second polariser. As noted above, rotation of the central polariser in practice allows light with a sinusoidal intensity versus rotation angle over 90°.

The O-ray and the E-ray travel through the birefringent material at different velocities (due to different refractive indices in the birefringent material). If this difference is sufficient and the path length through the birefringent material long enough then light at different wavelengths will become completely out of phase. Upon recombination at the second polariser, some colours will destructively interfere causing the light transmitted to be coloured.

The birefringence is described by equation (1):

$$\Delta n = n_x - n_y \qquad (1)$$

where $\Delta n$=birefringence, $n_x$=refractive index in the extraordinary plane and $n_y$=the refractive index in the ordinary plane.

The effect of birefringence is of "rotation" and interference of polarised light that is a product of the birefringence and the path length through the material.

Figure 12:
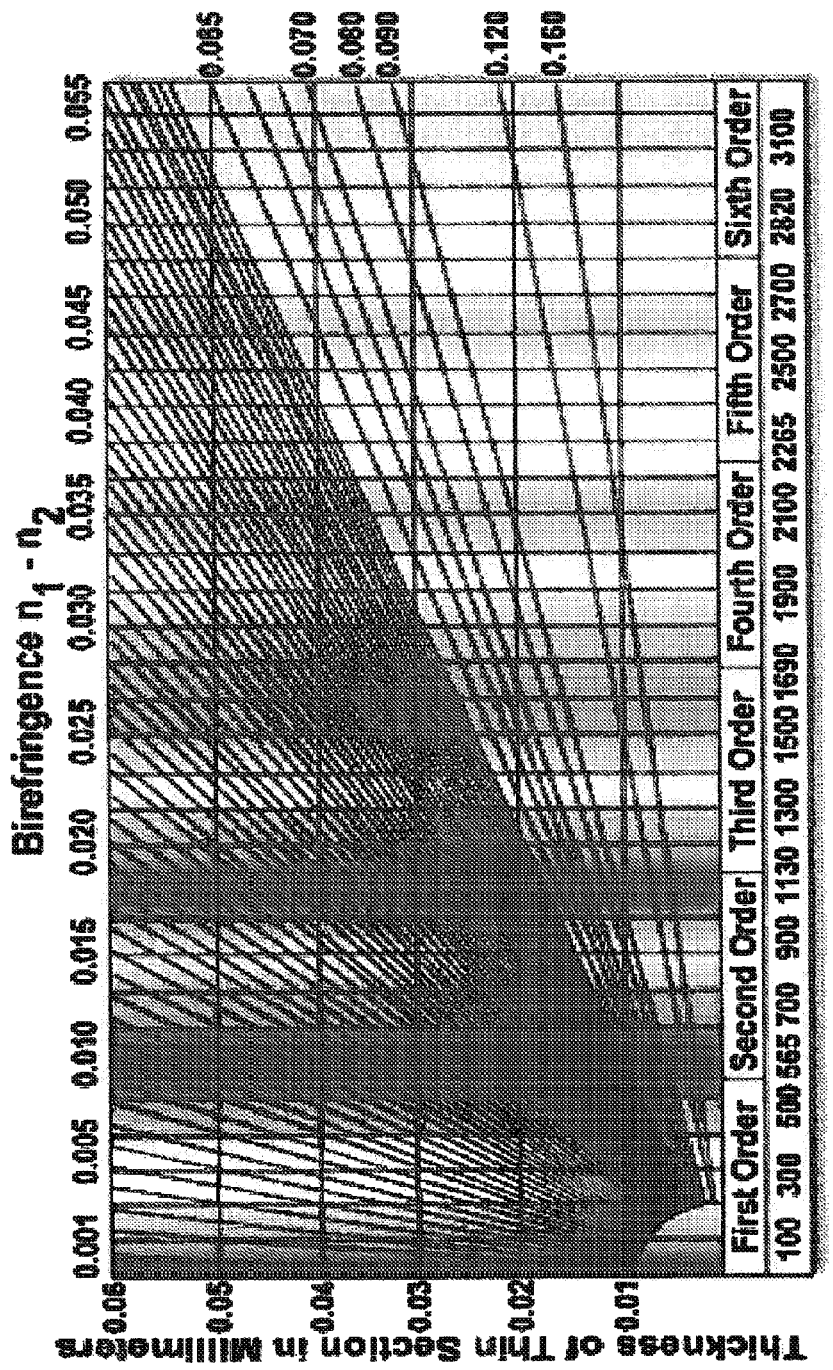
FIG. 12 illustrates a Michel-Levy chart.

A Michel-Lévy interference colour chart defines the interference colours from different orders of birefringence. An experimenter can use this chart to estimate a material's birefringence and also the material's retardation from comparison of transmitted light colour with the colours on the chart. Such a chart is illustrated in FIG. 12 for reference only. The chart is in black and white, and a full-colour version of the chart should be viewed to appreciate the colours of transmission.

The degree of retardation can be described by equation (2):

$$r = d\Delta n \qquad (2)$$

where: r=retardation (m), $\Delta n$=birefringence and d=path length (m)

For an approximately constant thickness of material, the path length d remains the same. Therefore measurement of the light passing through the material will indicate how birefringent the material is and therefore how much more oriented in one direction the material is as opposed to the other.

Birefringence is induced in transparent polymer films in three ways: crystal orientation, polymer chain orientation and crystal lattice deformation.

Refractive index is proportional to the density of a material; polymeric materials exist in two forms, crystalline and amorphous, both of which exist in a known proportion within a particular polymer type—polypropylene can be between 35% and 50% crystalline depending on its molecular weight range and its stereo-chemistry. During the bubble process crystallisation occurs as the molten cast tube (1 mm thick) is quenched using chilled water; cooling is rapid and temperature gradients occur across the thickness of the film giving some directionality to crystallisation. Crystalline areas form throughout the cast tubes that are then pulled during the stretching process into their final shape within the finished polymer. Birefringence is caused by differences in the lengths of the various dimensions of the crystalline regions and their orientation within the polymer; as the bubble polymer is stretched equally in both machine and transverse directions, this is expected to average out producing a low birefringence; however uneven distribution of crystalline areas causes variance of birefringence over distances of 1-3 mm.

Refractive index is also affected by the orientation of the polymer chains within the material; this has the largest effect on the overall birefringence which is proportional to the ratio between the machine direction and transverse direction stresses during stretching.

Finally, lattice deformation is theoretically a cause of birefringence but is unlikely to be significant in a soft, low melting point material such as polypropylene.

The resulting effect of the birefringence of a material manifests itself as a rotation of the polarisation angle of light being transmitted through the material; the effect is initiated via an interfacial interaction and propagated through the birefringent material; the degree of birefringence observed is a product of the initial interfacial interaction (i.e. the angle of incidence) and the subsequent path length through the material.

As noted above, the birefringent effect is a product of the thickness of the film and the degree to which the refractive indices differ between the two axes. The effect is visible if the film is placed between two crossed polarisers and rotated through 90° between a minima (equivalent to no change in transmission from the crossed polarisers) to a maxima at 45° where potentially as much light is transmitted as would be through a single polariser.

Birefringence in films is induced by orientation differences in production between the machine and the transverse direction; the resulting films have two axes at 90° to one another at which points the birefringence is at its minimum value, with 45° from either axis being the maximum. As a result of the nature of film processing in reels and sheets, every material produced by every known process will have the same properties including the polarisers.

Because of the universality of the orientation of polymers, a single measurement of birefringence at 45° is sufficient to determine the maximum value of any film and any printed product from that film. The polarisers themselves will also conform to this; therefore in the manufacture of a device such as this the specification for the polarisers should be that they should be cut at 45° from a master polariser sheet.

The method and apparatus disclosed in WO 2009/133390 involves the use of a pair of spinning polarisers that are at oriented at 90° to one another. The polarisers are operative to rotate at the same rate, and the apparatus is operative to measure the intensity of the light that passes through a sample placed between the polarisers.

To differentiate between a designated genuine film and others, the birefringence measurement method disclosed in WO 2009/1333390 may be employed to allow the user to eliminate other types of film, i.e. designated counterfeit films: BOPP film made by the stenter process is oriented more in the transverse direction than the machine direction, and so is considerably more birefringent than BOPP films made by the double bubble process. Birefringence can be controlled precisely using the double bubble process and so can provide a unique signature that can eliminate films.

The method of WO 2009/133390 allows a film to be securitized as is. The particular inherent characteristics of the film are observed using the disclosed method, and there is no need to add any further security or identifying features. This identification allows authentication for security purposes and also allows the film's origin to be determined.

The films referred to herein are generally sheet-form materials, and may be provided as individual sheets, or as a web material which may subsequently be processed (by die cutting for example) to provide sheet or article form materials. When referring to "film" in this specification it is intended, unless expressly provided otherwise, to include films in sheet, article or in web form.

As described above, the method of WO 2009/133390 is suitable for authenticating items containing films made by the bubble process. The bubble process results in films which have balanced orientation, well-defined and uniform thicknesses and other properties (high tensile strength, low elongation, high gloss and clarity, good puncture and flex-crack resistance, resistance to oils and greases, good water-impermeability) which define a "signature" of the film which indicate that it has been prepared by the bubble process.

In order to differentiate between films (e.g. BOPP films and others) the overall thickness of the film, as well as the thickness of individual layers, for example a laminating layer, may be measured. This allows determination of particular characteristics which are dependent on particular processes, for example a particular bubble process. Additionally, or alternatively, the unique birefringent signature of the film may be assessed and used to determine whether the film was made by a particular process and accordingly whether it is, for example, a genuine bank note or counterfeit. Birefringence depends on the anisotropy of the material and films made by bubble process have different anisotropies and hence different birefringent properties to films made by other processes. Furthermore the precise conditions used in the bubble process will affect the birefringent signature.

Thus WO 2009/133390 recognises that, rather than needing to add security or identification features, the inherent properties of films made by particular processes, such as the bubble process, are unique and act as a signature.

Actual counterfeit film is more likely to be bought rather than made by the counterfeiter. There are several sources that can be broken into three main groupings:

1. Cast or blown films—cast films are made by extruding polymer through a die onto a chilled roller. Blown films are made by extruding a polymer through a circular die and inflating a bubble in the semi-molten state. Cast films & blown films are typically either non or slightly oriented and so have inferior dimensional stability (i.e. they can easily be stretched), poorer optics and thickness control.

2. Mono oriented films—mono oriented films are made by extruding through a die and stretching in the machine direction. Mono oriented films are highly oriented; they have poorer optics and poor transverse direction dimensional stability.

3. Biaxially oriented films—biaxially oriented films are commercially available from Innovia Films Limited and from a number of other suppliers. Commercial grades of BOPP from many suppliers are generally made by the stenter process where PP is extruded through a slot die onto a chill roller, stretched in the machine direction over heated rollers and stretched in the transverse direction in a tenter frame. These films are anisotropic in nature unlike BOPP made by the double bubble process, which is stretch oriented evenly in all directions.

Whilst the method and apparatus of WO 2009/133390 have been satisfactory and will, it is believed, continue to be satisfactory for certain operating conditions, the applicant has recognised that it would be desirable to increase the range of operating conditions to allow for use of the method and apparatus in specific applications and/or environments and, potentially, for use in indicating authenticity of film types manufactured by other processes (e.g. genuine films formed by a stenter process). The applicant has also recognised that it would be desirable to increase an ability to discriminate between different film types having measureable properties which are similar, and to take account of films which are misaligned in the apparatus. The applicant has also recognised that it would be desirable to take account of variations in quality of authentic films to inhibit the chances of false negatives for BOPP bubble process films where the manufacturing process of those films is poorly controlled (or indeed for any other type of designated genuine film, regardless of the process by which it is manufactured).

The present invention has been devised with the foregoing considerations in mind.

According to an aspect of the present invention, there is provided an authentication apparatus operative to determine the authenticity of a polymer film, comprising an optically-based birefringence measuring arrangement operative to measure a first effect influenced by a birefringence characteristic of the film from a first angle comprising a non-normal angle to a plane of the film, and at least one of: a second angle; and a third angle; and wherein the apparatus is operative to: compare a value, or range of values, representative of the first effect as measured from the first angle with a value, or range of values representative of a specified first effect corresponding to a predetermined birefringence characteristic of an authentic polymer film for the first angle; compare a value, or range of values, representative of the first effect as measured from the at least one of the second and third angles with a value, or range of values representative of a specified first effect corresponding to a predetermined birefringence characteristic of an authentic polymer film for respective second and/or third angles; and output an authenticity signal indicative of authenticity or otherwise of the film based upon the comparisons.

The present invention allows a film to be securitized as is. The particular inherent characteristics of the film are observed in the present invention, and there is no need to add any further security or identifying features. This identification allows authentication for security purposes and also allows the film's origin to be determined. Additionally, the apparatus may be suitable to distinguish between films formed by a first process and those formed by other processes. For example, in cases where genuine items comprise substrates formed by the bubble process and where, in general, counterfeit items comprise substrates formed by the stenter or cast processes.

Optionally, the second angle may comprise a non-normal angle to a plane of the film and the third angle may comprise a normal angle to a plane of the film.

Optionally, the apparatus may be operative to differentiate between films made by a bubble process and films made by a different process.

Optionally, the optically-based birefringence measuring arrangement may comprise an emitter located, and operative, to illuminate a first side of the film located in a measuring region of the apparatus with electromagnetic radiation; a first polariser located between the first emitter and the first side of the film so that at least a portion of electromagnetic radiation emitted by the first emitter passes therethrough; a first detector located on a second side of the film, and operative to receive electromagnetic radiation from the emitter transmitted through the film and transmitted from the second side of the film at the first angle and at least one of the second and third angles; a second polariser located between the second side of the film and the first detector so that at least a portion of electromagnetic radiation transmitted through the film passes therethrough, wherein the first detector is operative to output a signal representative of the first effect as measured based upon electromagnetic radiation transmitted from the second side of the film at the first angle and at least one of the second and third angles.

Optionally, the first detector may be movable relative to the second side of the film for location at a first position to receive electromagnetic radiation from the emitter transmitted through the film and transmitted from the second side of the film at the first angle, and may be further movable to a second and/or third position to receive electromagnetic radiation from the emitter transmitted through the film and transmitted from the second side of the film at respective the second and/or third angles.

Optionally, the apparatus may further comprise: a second detector located on a second side of the film, and operative to receive electromagnetic radiation from the emitter transmitted through the film and transmitted from the second side of the film at the second angle; and/or a third detector located on a second side of the film, and operative to receive electromagnetic radiation from the emitter transmitted through the film and transmitted from the second side of the film at the third angle; wherein: the second detector is operative to output a signal representative of the first effect as measured based upon electromagnetic radiation transmitted from the second side of the film at the second angle; and/or the third detector is operative to output a signal representative of the first effect as measured based upon electromagnetic radiation transmitted from the second side of the film at the third angle.

Optionally, the first angle may comprise one of: (i) that described by vector [101] with respect to the film; and (ii) that described by vector [111] with respect to the film. Further optionally, the second angle may comprise the other of: (i) that described by vector [101] with respect to the film; and (ii) that described by vector [111] with respect to the film.

Optionally, an output signal output by the first detector may be proportional to an intensity of transmitted electromagnetic radiation received. Further optionally, an output signal output by the second detector and/or the third detector (where present) may be proportional to an intensity of transmitted electromagnetic radiation received.

Optionally, the first detector may be operative to communicate the output signal to a processor which is operative to compare a value of the output signal representative of the first effect as measured from the first angle with the value or range of values representative of a specified first effect corresponding to a predetermined birefringence characteristic of an authentic polymer film for the first angle. Further optionally, the second detector may be operative to communicate the output signal to a processor which is operative to compare a value of the output signal representative of the first effect as measured from the second angle with the value or range of values representative of a specified first effect corresponding to a respective predetermined birefringence characteristic of an authentic polymer film for the second angle; and/or the third detector may be operative to communicate the output signal to a processor which is operative to compare a value of the output signal representative of the first effect as measured from the third angle with the value or range of values representative of a specified first effect corresponding to a respective predetermined birefringence characteristic of an authentic polymer film for the third angle. Yet further optionally, the value or range of values may comprise at least one expected first detector output signal value representative of electromagnetic radiation transmitted from the second side of the film at the first angle and received by the first detector if an authentic film is located in the measuring region. Still further optionally, the value or range of values may comprise at least one expected second detector output signal value representative of electromagnetic radiation transmitted from the second side of the film and received by the second detector if an authentic film is located in the measuring region; and/or the value or range of values may comprise at least one expected third detector output signal value representative of electromagnetic radiation transmitted from the second side of the film and received by the third detector if an authentic film is located in the measuring region.

Optionally, the apparatus may further comprise an optically-based measuring arrangement operative to measure, at the first angle comprising a non-normal angle to a plane of the film, and at least one of the second angle and the third angle, a second effect influenced by at least one other optical characteristic of the film (e.g. transmissivity), and wherein the apparatus is operative to: compare a value, or range of values, representative of the second effect as measured at the first angle comprising a non-normal angle to a plane of the film, and at least one of the second angle and the third angle with a value, or range of values, representative of a specified second effect corresponding to a predetermined other optical characteristic of an authentic polymer film for a respective the first angle and respective second and/or third angles and output an authenticity signal indicative of authenticity or otherwise of the film based upon: a birefringence measurement comparison as described above or hereinafter; and/or the comparison of the value, or range of values, of the second effect as measured at the first angle comprising a non-normal angle to a plane of the film, and at least one of the second angle and the third angle with a respective value, or range of values, representative of the specified second effect corresponding to a predetermined other optical characteristic of an authentic polymer film for a respective the first angle and respective second and/or third angles.

Optionally, the second polariser may be controllably orientable so as to effect polarisation in one of: a first direction transverse to that of the first polariser; and a second direction the same as that of the first polariser; wherein the first detector, and/or optionally second and/or third detectors, is operative to measure the first effect influenced by the birefringence characteristic of the film when the second polariser is oriented so as to effect polarisation in the first direction transverse to that of the first polariser and to measure the second effect influenced by the other optical characteristic of the film when the second polariser is oriented so as to effect polarisation in the second direction the same as that of the first polariser.

Optionally, the first detector, and/or optionally second and/or third detectors, may be operative to output a first signal representative of the first effect as measured and to output a second signal representative of the second effect as measured. Further optionally, the first and second output signals output by the first detector, and/or optionally second and/or third detectors, may be proportional to an intensity of transmitted electromagnetic radiation received. Yet further optionally, the first detector, and/or optionally second and/or third detectors, may be operative to communicate the first and second output signals to a processor which is operative to: compare a value of the first output signal with a value, or range of values, representative of the specified first effect; and compare a value of the second output signal with a value, or range of values, representative of the specified second effect corresponding to a predetermined film transmissivity.

Optionally, if the first output signal value, or range of values, is of a level which is indistinguishable from a first output signal value, or range of values, representative of an effect influenced by background conditions, the processor may be operative to output the authenticity signal based upon a comparison of the value, or range of values, of the second output signal with the value, or range of values, representative of the specified second effect.

That is, if a comparison by the processor of the value of the first output signal with a value, or range of values, representative of a specified first effect corresponding to a predetermined birefringence characteristic of an authentic polymer film causes an inconclusive authenticity determination by the processor (because the first output signal value is, for example, very low, or indistinguishable from background noise), the processor may be operative to provide an authenticity determination indication based upon a comparison of the value of the second output signal with a value or range of values representative of the specified second effect (e.g. a predetermined film transmissivity).

Optionally, the value or range of values may comprise at least one expected first detector, and/or optionally second and/or third detectors, output signal value representative of electromagnetic radiation transmitted from the second side of the film and received by the first detector, and/or optionally second and/or third detectors, when the second polariser is oriented so as to effect polarisation in the first direction and in the second direction respectively if an authentic film is located in the measuring region.

Optionally, the processor may be further operative to: calculate a difference value between a value of the first output signal and a value of the second output signal; calculate a modified difference value by halving the difference value; calculate a birefringence representative value by subtracting the modified difference value from the second output signal value; compare the birefringence representative value to the value, or range of values, representative of the specified first effect; and output the authenticity signal indicative of authenticity or otherwise of the film based upon the comparison.

Optionally, the optically-based birefringence measuring arrangement may be further operative to measure a third effect influenced by the birefringence characteristic of the film over at least a portion of an electromagnetic spectrum and at the first angle and at least one of the second and third angles, and wherein the apparatus is operative to: compare a value, or range of values, representative of the third effect as measured at the first angle and at least one of the second and third angles with a respective value, or range of values, representative of a specified third effect corresponding to a predetermined birefringence characteristic of an authentic polymer film for a same at least a portion of an electromagnetic spectrum at a respective the first angle and respective second and/or third angles; and output an authenticity signal indicative of authenticity or otherwise of the film based upon the comparison.

Optionally, measurement of the third effect may comprise a monochromatic measurement (e.g. a colour measurement in which illuminating light of a particular colour is used).

Optionally, the first detector, and/or optionally second and/or third detectors, may be configured for selective response to the at least a portion of an electromagnetic spectrum.

Optionally, the first detector, and/or optionally second and/or third detectors, may be controllable to alter a detection range thereof to correspond to the at least a portion of an electromagnetic spectrum.

Optionally, the first detector, and/or optionally second and/or third detectors, may be pre-selected to detect electromagnetic radiation from the at least a portion of an electromagnetic spectrum.

Optionally, the first detector, and/or optionally each of second and/or third detectors, may comprise an array of at least two sub-detectors, a first of the at least two sub-detectors being operative to detect electromagnetic radiation from a first portion of an electromagnetic spectrum, and a second of the at least two sub-detectors being operative to detect electromagnetic radiation from a second portion of the electromagnetic spectrum.

Optionally, the first sub-detector may be controllable to alter a detection range thereof to correspond to the first portion of an electromagnetic spectrum, and the second sub-detector may be controllable to alter a detection range thereof to correspond to the second portion of an electromagnetic spectrum.

Optionally, the first sub-detector may be pre-selected to detect electromagnetic radiation from the first portion of an electromagnetic spectrum and the second sub-detector may be pre-selected to detect electromagnetic radiation from the second portion of an electromagnetic spectrum.

Optionally, the apparatus may further comprise at least one filter arranged to mask at least another portion of the electromagnetic spectrum and to transmit the at least a portion of an electromagnetic spectrum for reception by the first detector, and/or optionally second and/or third detectors.

Optionally, the emitter, or optionally emitters, may be controllable to emit electromagnetic radiation in the at least a portion of an electromagnetic spectrum.

Optionally, the emitter, or optionally emitters, may be pre-selected to emit electromagnetic radiation in the at least a portion of an electromagnetic spectrum.

Optionally, the emitter, or optionally emitters, may be operative in a first mode to emit white-light and in a second mode to emit coloured light.

Optionally, the apparatus may be operative in a first mode to control a first emitter to emit white-light and in a second mode to control a second emitter to emit coloured light.

Optionally, in the first mode the apparatus may be operative to indicate if the polymer film under test comprises a polymer film of a first genuine type or at least a second genuine type based upon an output signal of the first detector, and further wherein, responsive to an output signal indicating that the polymer under test is of a type other than the first genuine type, the apparatus is operative to implement the second mode and to indicate if the polymer film under test comprises a polymer film of the at least a second genuine type or otherwise based upon the output signals of the first detector in both the first and second modes.

Optionally, in the first mode the apparatus may be operative to: compare the value, or range of values, representative of the third effect as measured at the first angle and at least one of the second and third angles with the value, or range of values, representative of a specified third effect corresponding to a predetermined birefringence characteristic of a polymer film of a first genuine type at a respective the first angle and respective second and/or third angles; and output a classification signal indicative of the film comprising a first genuine type or otherwise based upon the comparison.

Optionally, the apparatus may be operative to output a classification signal indicative of the film comprising a first genuine type if the value representative of the third effect as measured at the first, second or third angle is lower than a corresponding first mode first threshold value for the first, second or third angle representative of an upper limit for the specified first effect for a film of the first genuine type.

Optionally, the apparatus may be operative to output a classification signal indicative of the film comprising a non-genuine type if the value representative of the third effect as measured at the first, second or third angle is both higher than the corresponding first mode first threshold value for the first, second or third angle and outside a range of values between a corresponding first mode second threshold value for the first, second or third angle and a corresponding first mode third threshold value for the first, second or third angle.

Optionally, the apparatus may be operative to implement the second mode if the value representative of the third effect as measured at the first, second or third angle in the first mode is between the corresponding first mode second threshold value for the first, second or third angle and the corresponding first mode third threshold value for the first, second or third angle.

Optionally, the apparatus may be operative to output a classification signal indicative of the film comprising a second genuine type if the value representative of the third effect as measured at the first, second or third angle is within a range of values between a corresponding second mode first threshold value for the first, second or third angle and a corresponding second mode second threshold value for the first, second or third angle, the range of values representative of a specified third effect for a film of the second genuine type.

Optionally, the apparatus may further comprise an optically-based birefringence imaging arrangement for imaging a birefringence pattern of the film at the first angle and at least one of the second and third angles, and wherein the apparatus is operative to: compare an image of the birefringence pattern with a respective image representative of a predetermined birefringence pattern of an authentic polymer film at a respective the first angle and respective the second and third angles; and output an authenticity signal indicative of authenticity or otherwise of the film based upon the comparison.

Optionally, the optically-based birefringence imaging arrangement may comprise an emitter located, and operative, to illuminate a first side of the film located in a measuring region of the apparatus with electromagnetic radiation; a first polariser located between the first emitter and the first side of the film so that at least a portion of electromagnetic radiation emitted by the first emitter passes therethrough; an imaging device located on a second side of the film, and operative to receive electromagnetic radiation from the emitter transmitted through the film and transmitted from the second side of the film; a second polariser located between the second side of the film and the imaging device so that at least a portion of electromagnetic radiation transmitted through the film passes therethrough, wherein the imaging device is operative to output data representative of an imaged birefringence pattern based upon electromagnetic radiation transmitted from the second side of the film and received at the imaging device.

Optionally, the imaging device may be operative to output the data representative of an imaged birefringence pattern to a processor which is operative to compare the output data with a data-set representative of a predetermined birefringence pattern.

Optionally, at least one of: the emitter; the first polariser; and the second polariser may be common with that/those of the optically-based birefringence measuring arrangement and/or of the optically-based measuring arrangement.

Optionally, the emitter may comprise a white-light source.

Optionally, the imaging device may comprise a photosensitive array.

Optionally, the apparatus may further comprise an optical response modifier arranged to modify the first effect to introduce an offset of a predetermined amount to the value, or range of values, representative of the effect as measured, wherein the optically-based birefringence measuring arrangement is operative to measure the first effect as modified.

Optionally, the optical response modifier may be located in a beam path of electromagnetic radiation between the emitter and the first detector, and/or optionally second and/or third detectors, and further wherein the first detector, and/or optionally second and/or third detectors, may be operative to measure the first effect.

Optionally, the first detector, and/or optionally second and/or third detectors, may be operative to output a signal representative of the first effect as modified.

Optionally, the first detector, and/or optionally second and/or third detectors, may be operative to communicate the output signal to a processor which may be operative to compare a value of the output signal representative of the first effect as modified with a value or range of values representative of a specified first effect corresponding to a predetermined birefringence characteristic of an authentic polymer film and as modified by a same optical response modifier.

Optionally, the apparatus may be operative to receive an item comprising a polymer film forming at least a portion of a substrate of the item.

According to another aspect of the present invention, there is provided a banknote authentication apparatus comprising an apparatus including any one or more of the features described above, wherein the apparatus is operative to determine the authenticity of a banknote comprising a polymer film forming at least a portion of a substrate of the banknote.

The apparatus comprising any one or more of the features as described above may be used to determine the authenticity of a polymer film.

According to another aspect of the present invention, there is provided a method of determining the authenticity of a polymer film, comprising: measuring a first effect influenced by a birefringence characteristic of the film from a first angle comprising a non-normal angle to a plane of the film, and at least one of: a second angle; and a third angle; comparing a value, or range of values, representative of the first effect as measured from the first angle with a value, or range of values representative of a specified first effect corresponding to a predetermined birefringence characteristic of an authentic polymer film for the first angle; comparing a value, or range of values, representative of the first effect as measured from the at least one of the second and third angles with a value, or range of values representative of a specified first effect corresponding to a predetermined birefringence characteristic of an authentic polymer film for respective second and/or third angles; and outputting an authenticity signal indicative of authenticity or otherwise of the film based upon the comparisons.

Optionally, the second angle may be a non-normal angle to a plane of the film and the third angle may be a normal angle to a plane of the film.

Optionally, the method may further comprise indicating if the polymer film is made by a bubble process or by a different process.

Optionally, the method may further comprise: illuminating a first side of the film located in a measuring region of the apparatus with electromagnetic radiation polarised by a first polariser located between a first emitter and the first side of the film so that at least a portion of electromagnetic radiation emitted by the first emitter passes therethrough; receiving, at a first detector located on a second side of the film, electromagnetic radiation from the emitter transmitted through the film at the first angle and at least one of the second and third angles and polarised by a second polariser located between the second side of the film and the first detector; and outputting a signal representative of the first effect as measured based upon electromagnetic radiation transmitted from the second side of the film at the first angle and at least one of the second and third angles.

Optionally, the method may further comprise locating the first detector at a first position to receive electromagnetic radiation from the emitter transmitted through the film and transmitted from the second side of the film at the first angle, and moving the first detector to a second and/or third position to receive electromagnetic radiation from the emitter transmitted through the film and transmitted from the second side of the film at respective the second and/or third angles.

Optionally, the method may further comprise: providing a second detector on a second side of the film for receiving electromagnetic radiation from the emitter transmitted through the film and transmitted from the second side of the film at the second angle; and/or providing a third detector located on a second side of the film for receiving electromagnetic radiation from the emitter transmitted through the film and transmitted from the second side of the film at the third angle; and outputting, from the second detector, a signal representative of the first effect as measured based upon electromagnetic radiation transmitted from the second side of the film at the second angle; and/or outputting, from the third detector, a signal representative of the first effect as measured based upon electromagnetic radiation transmitted from the second side of the film at the third angle.

Optionally, the first angle may comprise one of: (i) that described by vector [101] with respect to the film; and (ii) that described by vector [111] with respect to the film. Further optionally, the second angle may comprise the other of: (i) that described by vector [101] with respect to the film; and (ii) that described by vector [111] with respect to the film.

Optionally, the method may further comprise: communicating the output signal to a processor; comparing a value of the output signal representative of the first effect as measured from the first angle with the value or range of values representative of a specified first effect corresponding to a predetermined birefringence characteristic of an authentic polymer film for the first angle.

Optionally, the value or range of values may comprise at least one expected first detector output signal value representative of electromagnetic radiation transmitted from the second side of the film at the first angle and received by the first detector if an authentic film is located in the measuring region.

Optionally, an output signal output by the second detector and/or the third detector may be proportional to an intensity of transmitted electromagnetic radiation received.

Optionally, the method may further comprise: communicating the output signal from the second detector to the processor; comparing a value of the output signal representative of the first effect as measured from the second angle with the value or range of values representative of a specified first effect corresponding to a respective predetermined birefringence characteristic of an authentic polymer film for the second angle; and/or communicating the output signal from the third detector to the processor; comparing a value of the output signal representative of the first effect as measured from the third angle with the value or range of values representative of a specified first effect corresponding to a respective predetermined birefringence characteristic of an authentic polymer film for the third angle.

Optionally, the value or range of values may comprise at least one expected second detector output signal value representative of electromagnetic radiation transmitted from the second side of the film and received by the second detector if an authentic film is located in the measuring region; and/or the value or range of values may comprise at least one expected third detector output signal value representative of electromagnetic radiation transmitted from the second side of the film and received by the third detector if an authentic film is located in the measuring region.

Optionally, the method may further comprise: measuring, at the first angle comprising a non-normal angle to a plane of the film, and at least one of the second angle and the third angle, a second effect influenced by at least one other optical characteristic of the film; comparing a value, or range of values, representative of the second effect as measured at the first angle and at least one of the second angle and the third angle, with a value, or range of values, representative of a specified second effect corresponding to a predetermined other optical characteristic of an authentic polymer film at a respective the first angle and a respective the second angle and/or third angle; and outputting an authenticity signal indicative of authenticity or otherwise of the film based upon: a birefringence measurement comparison as described above or hereinafter; and/or the comparison of the value, or range of values, of the second effect as measured at the first angle and at least one of the second and third angles with a respective value, or range of values, representative of the specified second effect corresponding to a predetermined other optical characteristic at a respective the first angle and respective second and/or third angles.

Optionally, the method may further comprise: orienting the second polariser so as to effect polarisation in one of: a first direction transverse to that of the first polariser; and a second direction the same as that of the first polariser; measuring the first effect influenced by the birefringence characteristic of the film when the second polariser is oriented so as to effect polarisation in the first direction transverse to that of the first polariser and measuring the second effect influenced by the other optical characteristic of the film when the second polariser is oriented so as to effect polarisation in the second direction the same as that of the first polariser.

Optionally, the method may further comprise outputting a first signal representative of the first effect as measured and outputting a second signal representative of the second effect as measured.

Optionally, the first and second output signals output by the first detector, and/or optionally second and/or third detectors, may be proportional to an intensity of transmitted electromagnetic radiation received.

Optionally, the method may further comprise: communicating the first and second output signals to a processor; comparing a value of the first output signal with a value, or range of values, representative of the specified first effect; and comparing a value of the second output signal with a value, or range of values, representative of the specified second effect corresponding to a predetermined film transmissivity.

Optionally, if the first output signal value, or range of values, is of a level which may be indistinguishable from a first output signal value, or range of values, representative of an effect influenced by background conditions, the processor is operative to output the authenticity signal based upon a comparison of the value, or range of values, of the second output signal with the value, or range of values, representative of the specified second effect.

Optionally, the value or range of values may comprise at least one expected first detector, and/or optionally second and/or third detectors, output signal value representative of electromagnetic radiation transmitted from the second side of the film and received by the first detector, and/or optionally second and/or third detectors, when the second polariser is oriented so as to effect polarisation in the first direction and in the second direction respectively if an authentic film is located in the measuring region.

Optionally, the method may further comprise: calculating a difference value between a value of the first output signal and a value of the second output signal; calculating a modified difference value by halving the difference value; calculating a birefringence representative value by subtracting the modified difference value from the second output signal value; comparing the birefringence representative value to the value, or range of values, representative of the specified first effect; and outputting the authenticity signal indicative of authenticity or otherwise of the film based upon the comparison.

Optionally, the method may further comprise: measuring a third effect influenced by the birefringence characteristic of the film over at least a portion of an electromagnetic spectrum and at the first angle and at least one of the second angle and the third angle; comparing a value, or range of values, representative of the third effect as measured at the first angle and the second and/or third angles with a respective value, or range of values, representative of a specified third effect corresponding to a predetermined birefringence characteristic of an authentic polymer film for a same at least a portion of an electromagnetic spectrum at a respective the first angle and respective the second and/or third angles; and outputting an authenticity signal indicative of authenticity or otherwise of the film based upon the comparison.

Optionally, measurement of the third effect may comprise a monochromatic measurement.

Optionally, the method may further comprise configuring the first detector, and/or optionally second and/or third detectors, for selective response to the at least a portion of an electromagnetic spectrum.

Optionally, the method may further comprise controlling the first detector, and/or optionally second and/or third detectors, to alter a detection range thereof to correspond to the at least a portion of an electromagnetic spectrum.

Optionally, the method may further comprise pre-selecting the first detector, and/or optionally second and/or third detectors, to detect electromagnetic radiation from the at least a portion of an electromagnetic spectrum.

Optionally, the method may further comprise providing an array of at least two sub-detectors as the first detector, and/or optionally each of second and/or third detectors; and detecting, at a first of the at least two sub-detectors, electromagnetic radiation from a first portion of an electromagnetic spectrum; detecting, at a second of the at least two sub-detectors, electromagnetic radiation from a second portion of the electromagnetic spectrum.

Optionally, the method may further comprise controlling the first sub-detector to alter a detection range thereof to correspond to the first portion of an electromagnetic spectrum, and controlling the second sub-detector to alter a detection range thereof to correspond to the second portion of an electromagnetic spectrum.

Optionally, the method may further comprise pre-selecting the first sub-detector to detect electromagnetic radiation from the first portion of an electromagnetic spectrum and the second sub-detector to detect electromagnetic radiation from the second portion of an electromagnetic spectrum.

Optionally, the method may further comprise masking at least another portion of the electromagnetic spectrum to transmit the at least a portion of an electromagnetic spectrum for reception by the first detector, and/or optionally second and/or third detectors.

Optionally, the method may further comprise controlling the emitter, or optionally emitters, to emit electromagnetic radiation in the at least a portion of an electromagnetic spectrum.

Optionally, the method may further comprise pre-selecting the emitter, or optionally emitters, to emit electromagnetic radiation in the at least a portion of an electromagnetic spectrum.

Optionally, the method may further comprise operating the emitter, or optionally emitters, in a first mode to emit white-light and in a second mode to emit coloured light.

Optionally, the method may further comprise: controlling a first emitter in a first mode to emit white-light; and controlling a second emitter in a second mode to emit coloured light.

Optionally, the method may comprise, in the first mode, indicating if the polymer film under test comprises a polymer film of a first genuine type or at least a second genuine type based upon an output signal of the first detector, and/or optionally second and/or third detectors, and further wherein, responsive to an output signal indicating that the polymer under test is of a type other than the first genuine type, implementing the second mode and indicating if the polymer film under test comprises a polymer film of the at least a second genuine type or otherwise based upon the output signals of the first detector in both the first and second modes, and/or optionally output signals of the second and/or third detectors in both the first and second modes.

Optionally, in the first mode the method may further comprise the steps of: comparing the value, or range of values, representative of the third effect as measured at the first angle and the second and/or third angles with the value, or range of values, representative of a specified third effect corresponding to a predetermined birefringence characteristic of a polymer film of a first genuine type at a respective the first angle and respective second and/or third angles; and outputting a classification signal indicative of the film comprising a first genuine type or otherwise based upon the comparison.

Optionally, the method may further comprise outputting a classification signal indicative of the film comprising a first genuine type if the value representative of the third effect as measured at the first angle and the second and/or third angles is lower than a corresponding first mode first threshold value for the first, second or third angle representative of an upper limit for the specified first effect for a film of the first genuine type.

Optionally, the method may further comprise outputting a classification signal indicative of the film comprising a non-genuine type if the value representative of the third effect as measured at the first angle and the second and/or third angles is both higher than the corresponding first mode first threshold value for the first, second or third angle and outside a range of values between a corresponding first mode second threshold value for the first, second or third angle and a corresponding first mode third threshold value for the first, second or third angle.

Optionally, the method may further comprise implementing the second mode if the value representative of the third effect as measured at the first angle and the second and/or third angle in the first mode is between the corresponding first mode second threshold value for the first, second or third angle and the first mode third threshold value for the first, second or third angle.

Optionally, the method may further comprise outputting a classification signal indicative of the film comprising a second genuine type if the value representative of the third effect as measured at the first, second or third angle is within a range of values between a corresponding second mode first threshold value for the first, second or third angle and a corresponding second mode second threshold value for the first, second or third angle, the range of values representative of a specified third effect for a film of the second genuine type.

Optionally, the method may further comprise: imaging a birefringence pattern of the film at the first angle and at least one of the second and/or third angles; comparing an image of the birefringence pattern at the first, second or third angle with a respective image representative of a predetermined birefringence pattern of an authentic polymer film at a corresponding first, second and third angle; and outputting an authenticity signal indicative of authenticity or otherwise of the film based upon the comparison.

Optionally, the method may further comprise outputting, from an imaging device, data representative of an imaged birefringence pattern to a processor and comparing the output data with a data-set representative of a predetermined birefringence pattern.

Optionally, the method may further comprise illuminating the film using an emitter comprising a white-light source.

Optionally, the method may further comprise providing a photosensitive array to implement the imaging step.

Optionally, the method may further comprise modifying the first effect to introduce an offset of a predetermined amount to the value, or range of values, representative of the first effect as measured at the first angle at the second and/or third angles, and measuring the first effect as modified.

Optionally, the method may further comprise communicating, from the first detector, and/or optionally second and/or third detectors, the output signal to a processor and comparing a value of the output signal representative of the first effect as modified with a value, or range of values, representative of a specified first effect corresponding to a predetermined birefringence characteristic of an authentic polymer film and as modified by a same optical response modifier.

According to another aspect of the present invention, there is provided a computer program comprising computer program elements operative in a computer processor to implement one or more aspects of an authentication apparatus as described above and hereinafter.

According to another aspect of the present invention, there is provided a computer program comprising computer program elements operative in a computer processor to implement one or more aspects of a method as described above and hereinafter.

According to another aspect of the present invention, there is provided a computer readable medium carrying a computer program as described above.

One or more specific embodiments in accordance with aspects of the present invention will be described, by way of example only, and with reference to the following drawings.

Figure 5:
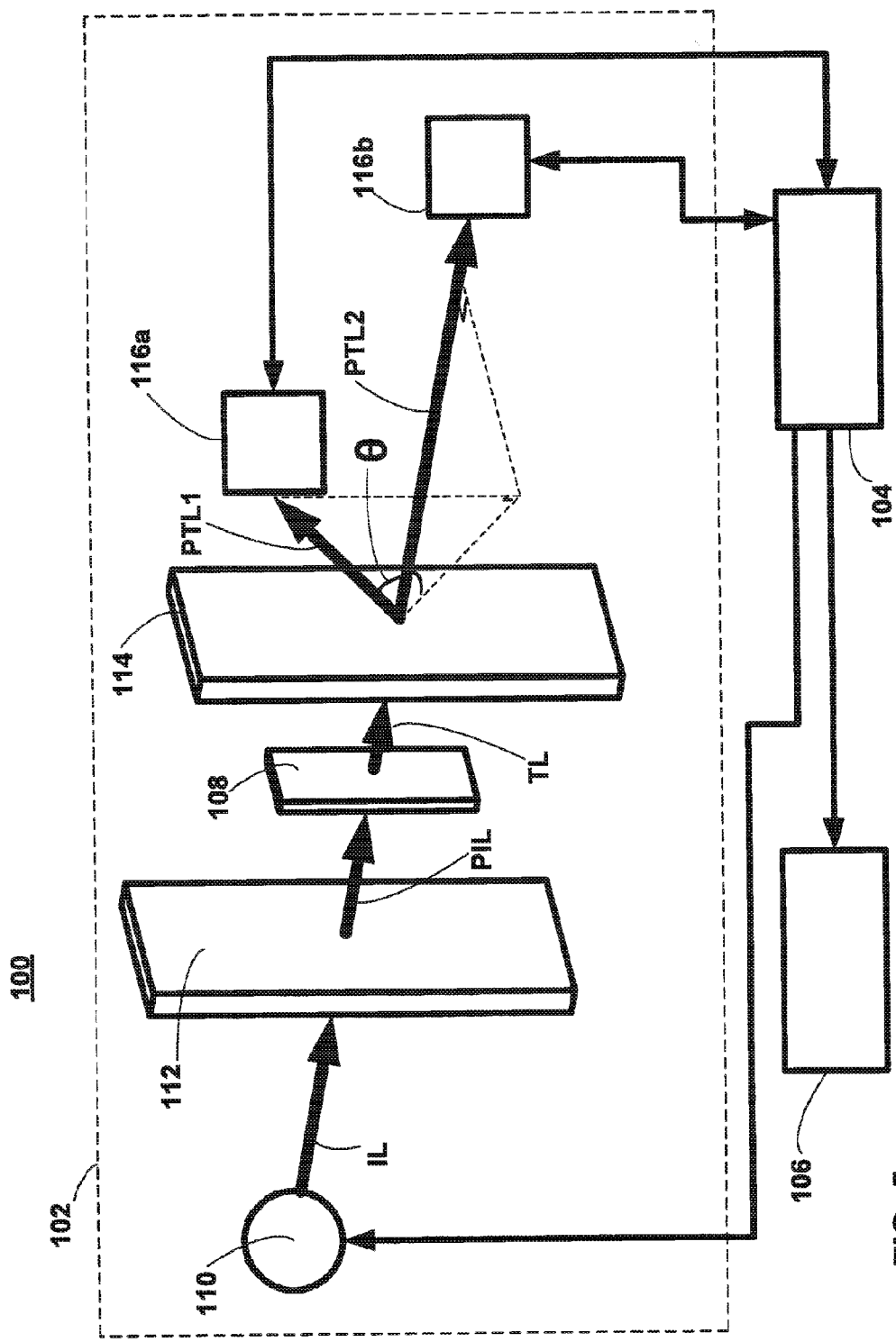
FIG. 5 schematically illustrates a perspective view of the authentication apparatus of FIGS. 4a to 4d in an optional arrangement.
Figure 6:
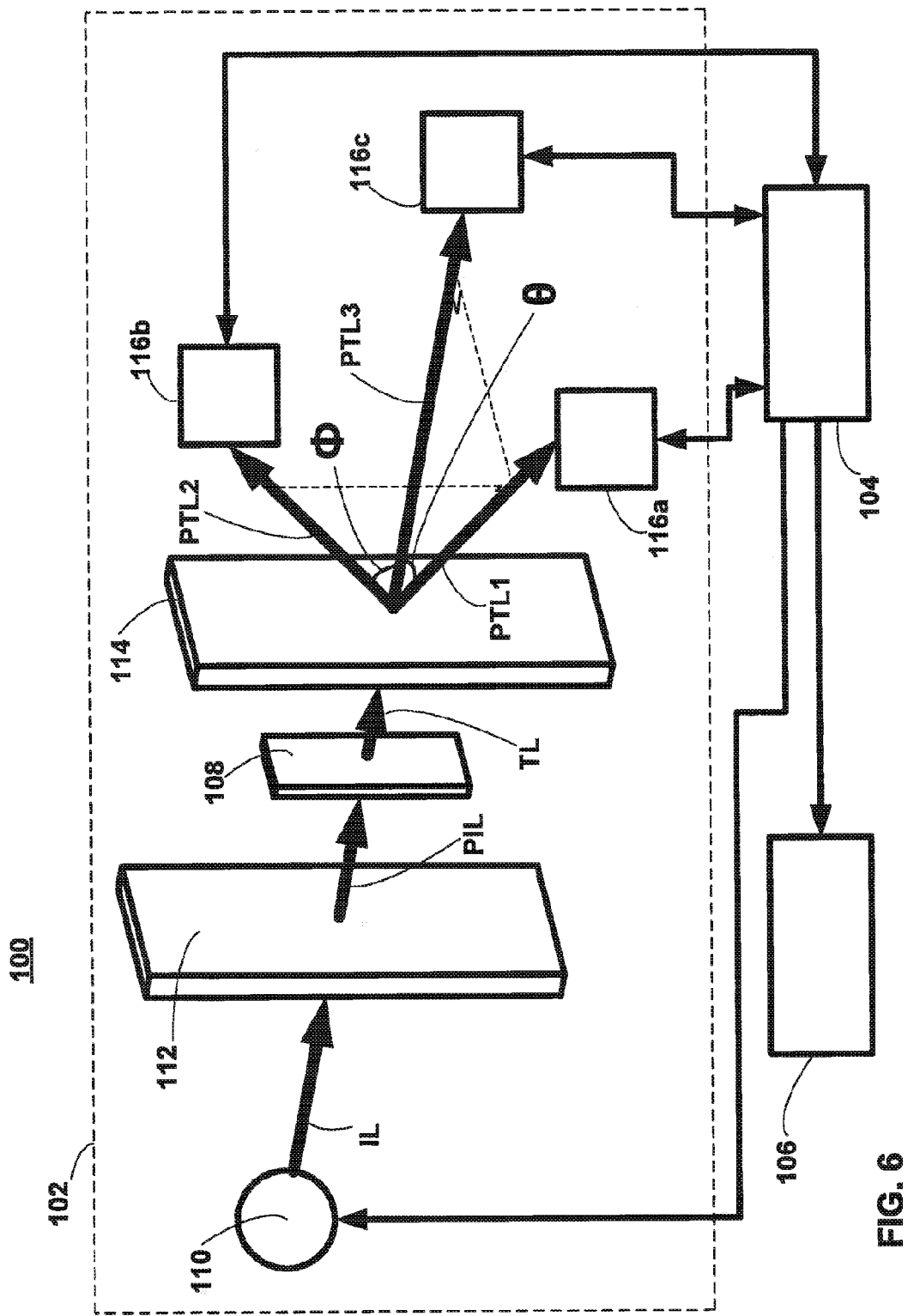
FIG. 6 schematically illustrates a perspective view of the authentication apparatus of FIGS. 4a to 4d in another optional arrangement.
Figure 7A:
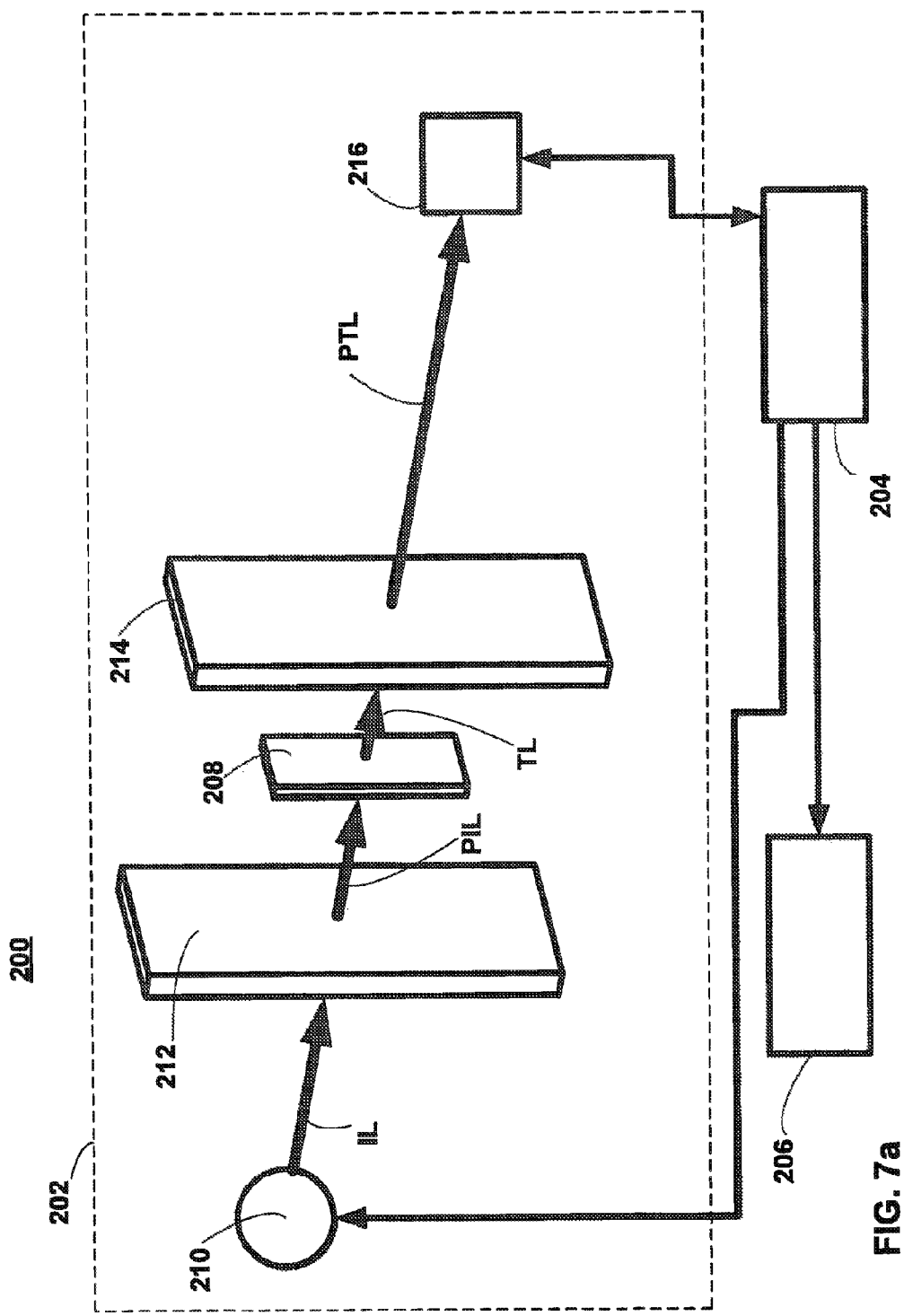
FIGS. 7a and 7b schematically illustrate perspective views of another authentication apparatus in accordance with one or more embodiments of the present invention.
Figure 7B:
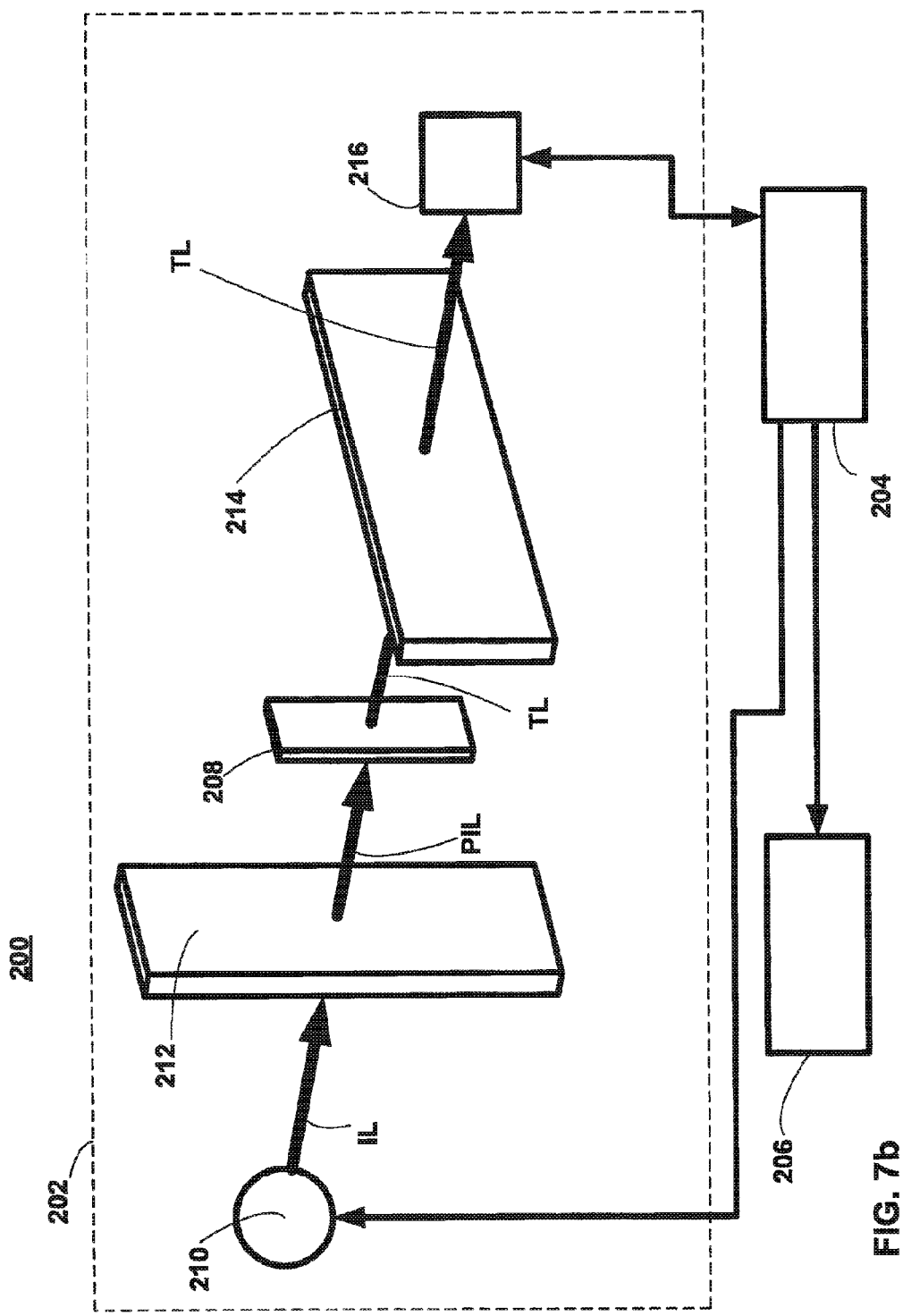
Figure 8:
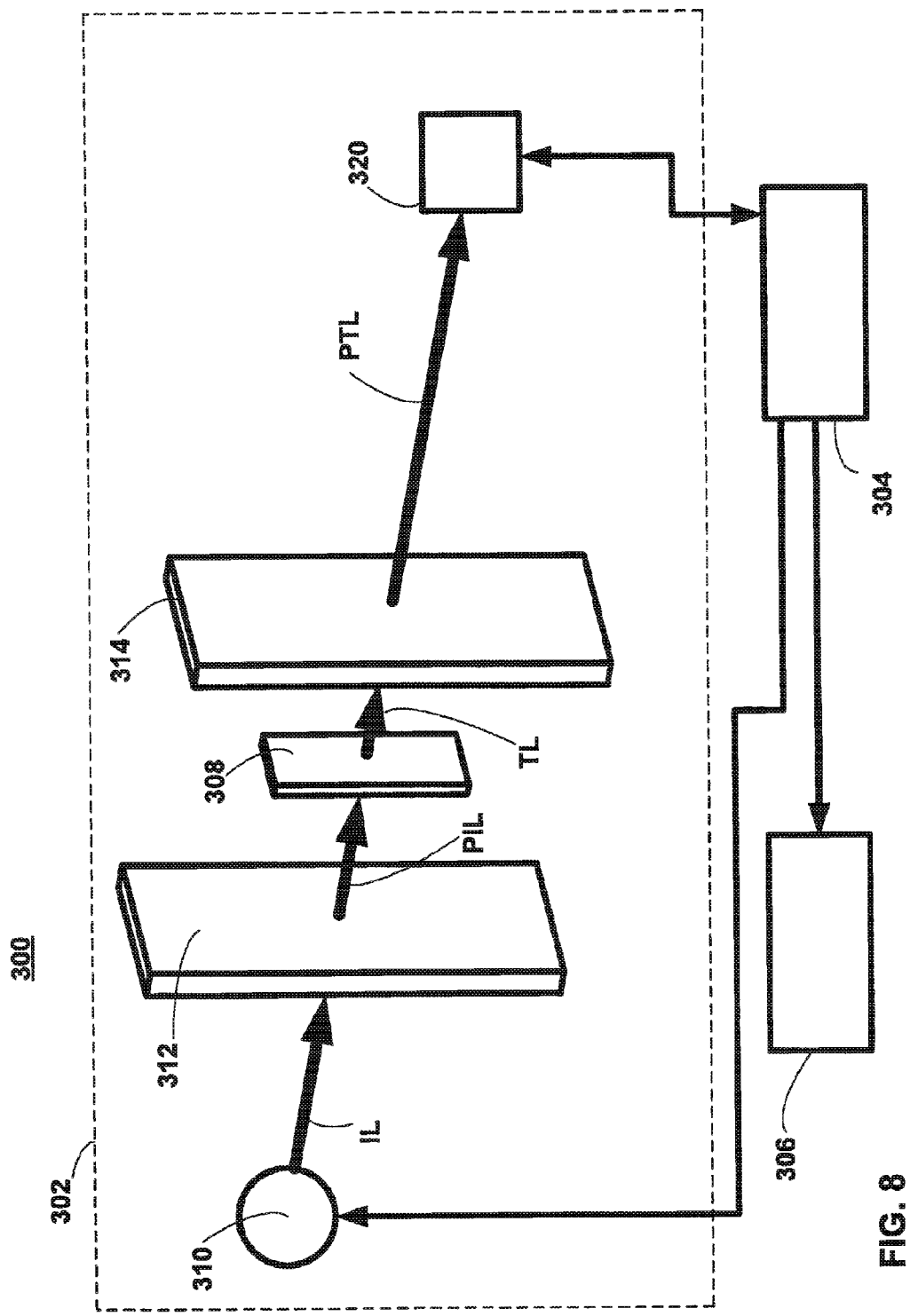
FIG. 8 schematically illustrates a perspective view of a further authentication apparatus in accordance with one or more embodiments of the present invention.
Figure 9:
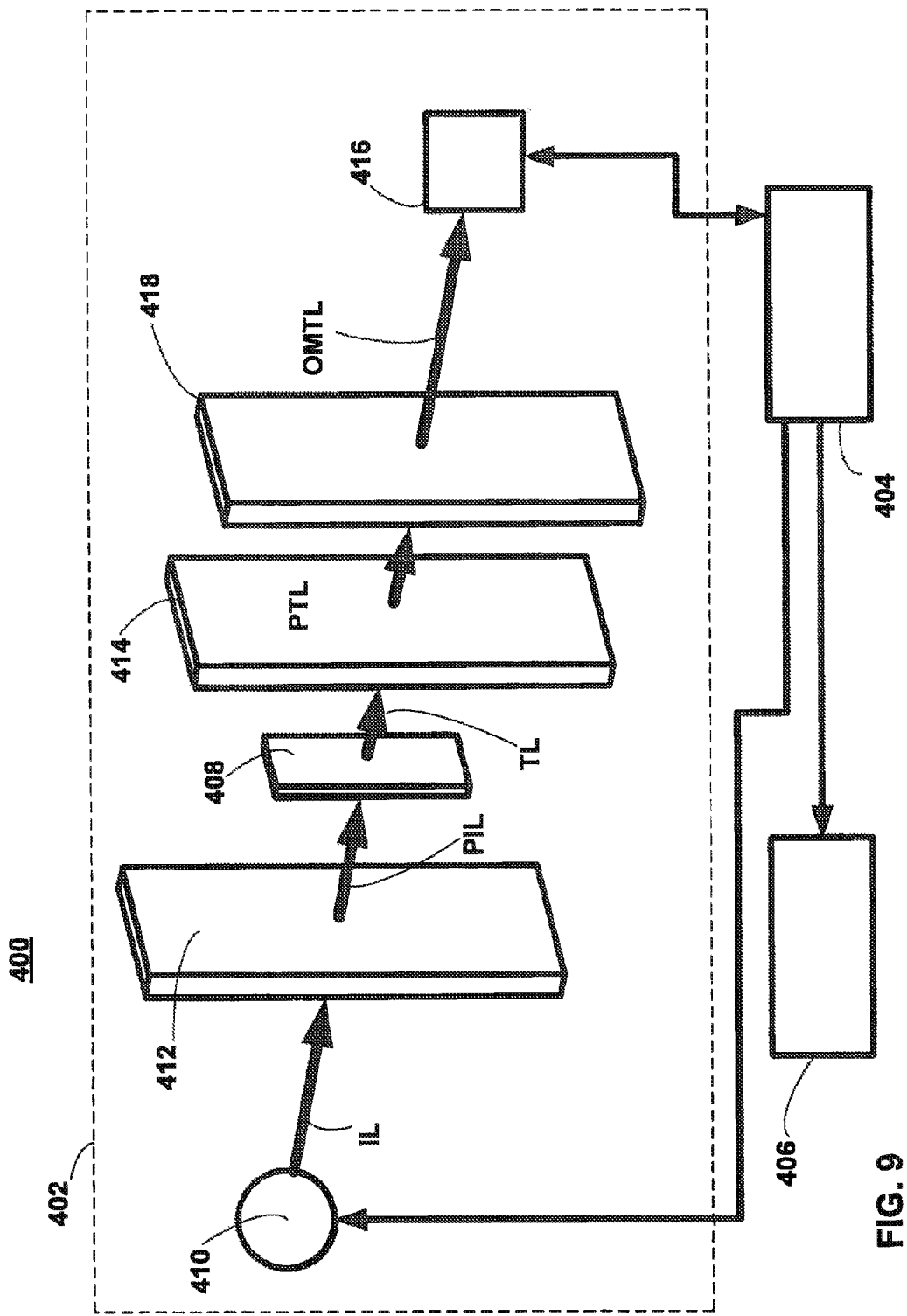
FIG. 9 schematically illustrates a perspective view of yet another authentication apparatus in accordance with one or more embodiments of the present invention.
Figure 10:
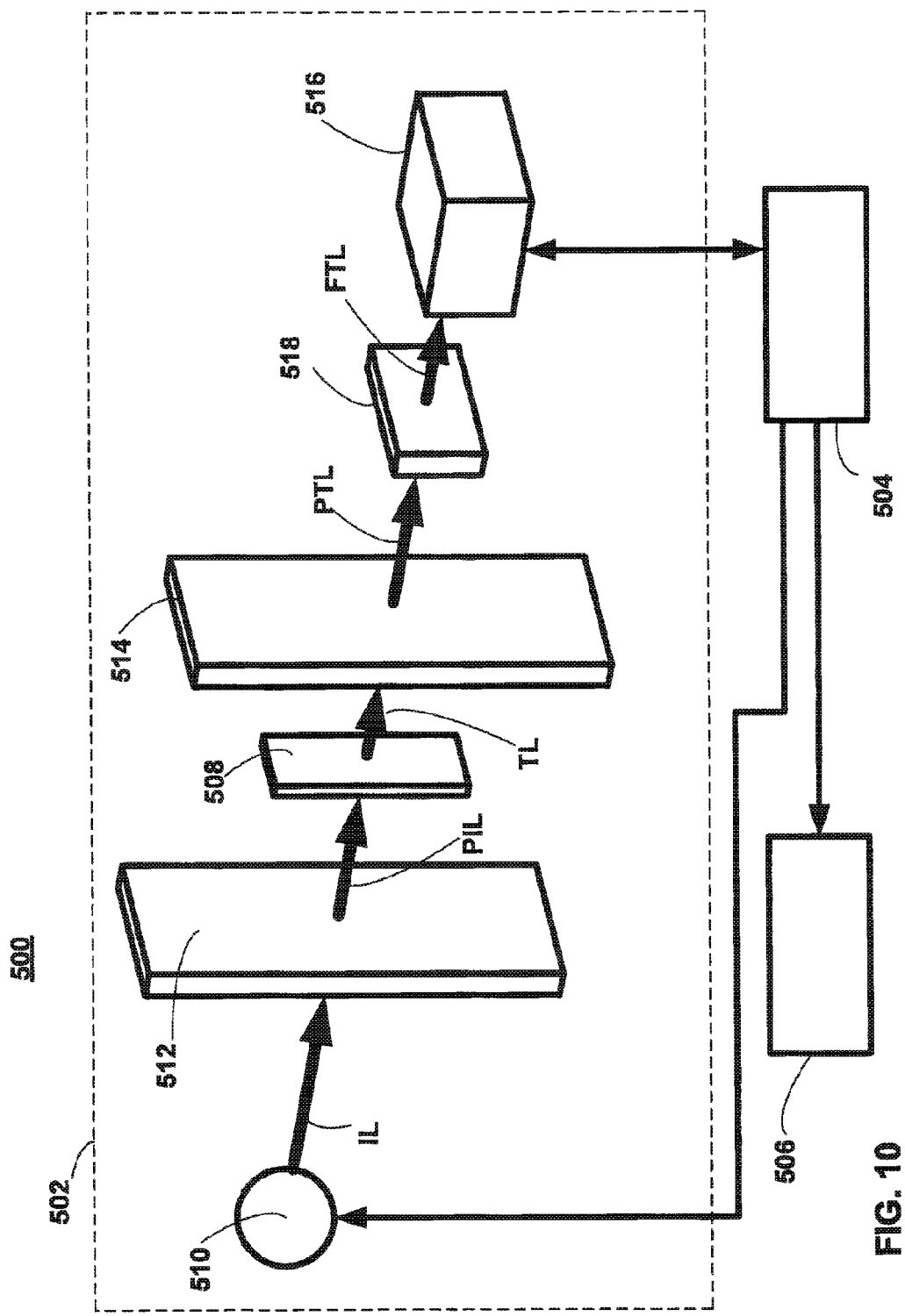
FIG. 10 schematically illustrates a perspective view of yet another authentication apparatus in accordance with one or more embodiments of the present invention.
Figure 11:
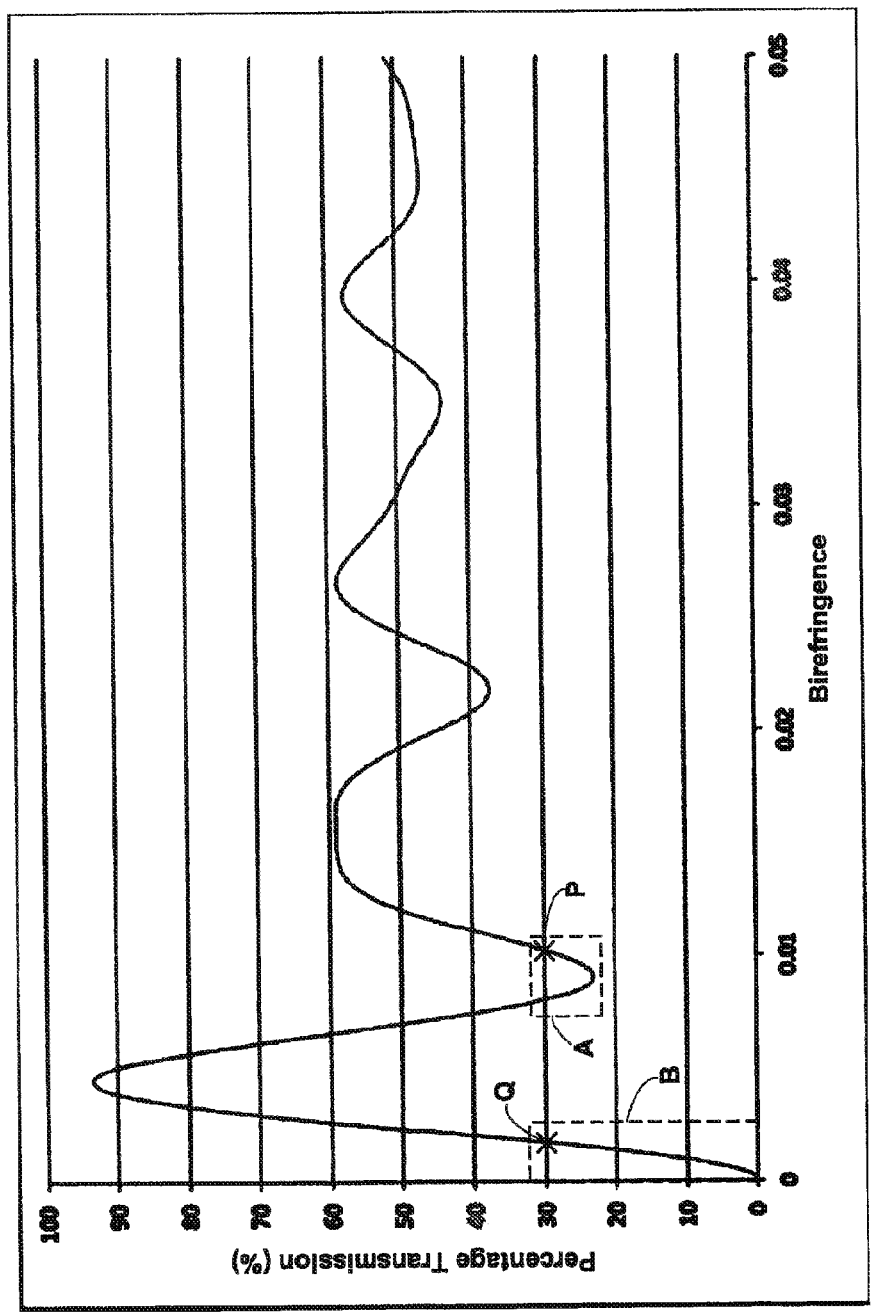
FIG. 11 illustrates a graph of birefringence versus percentage transmission for a 60 μm BOPP film.
Figure 13:
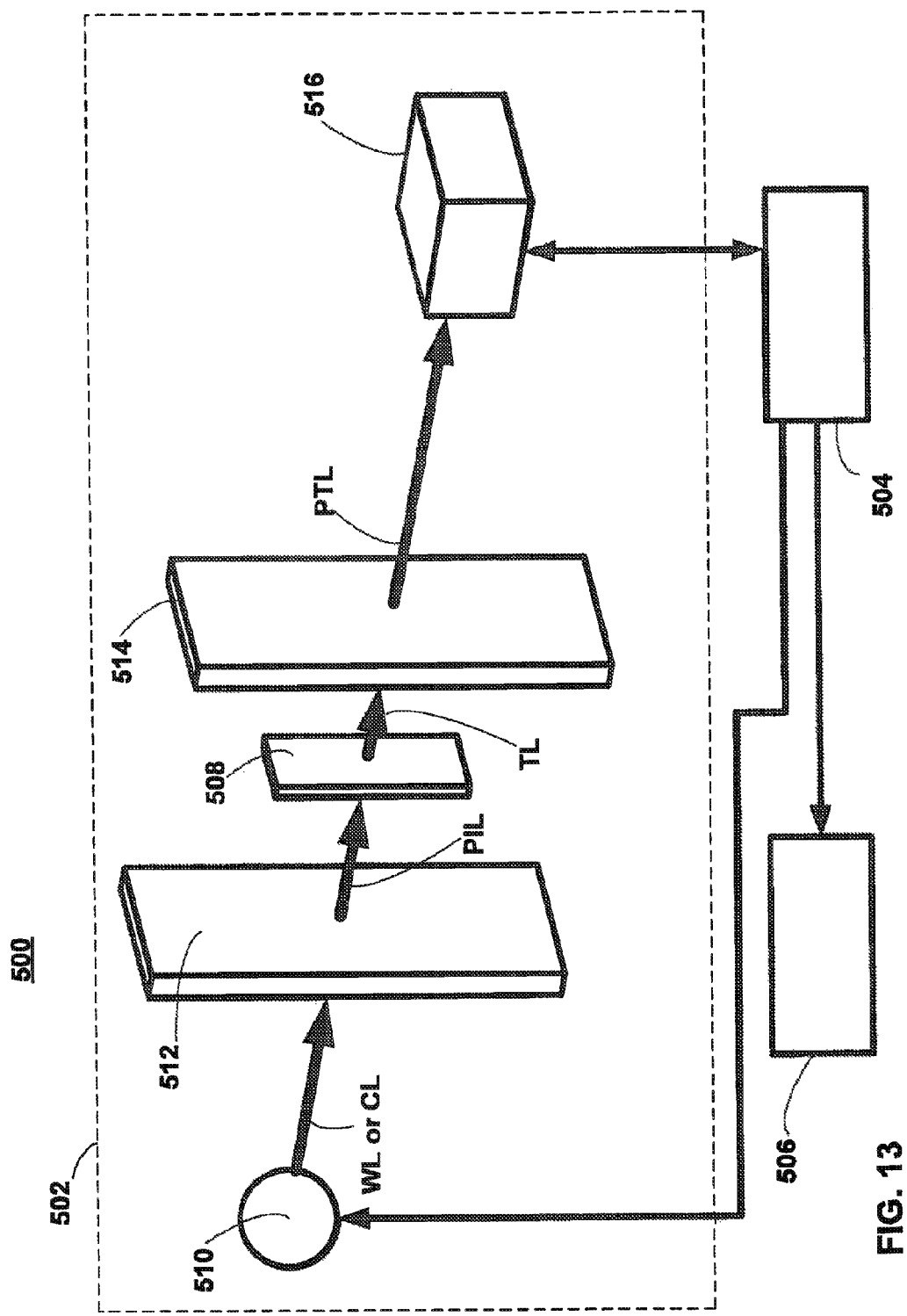
FIG. 13 schematically illustrates a perspective view of an optional arrangement of the apparatus illustrated in FIG. 10.
Figure 14:
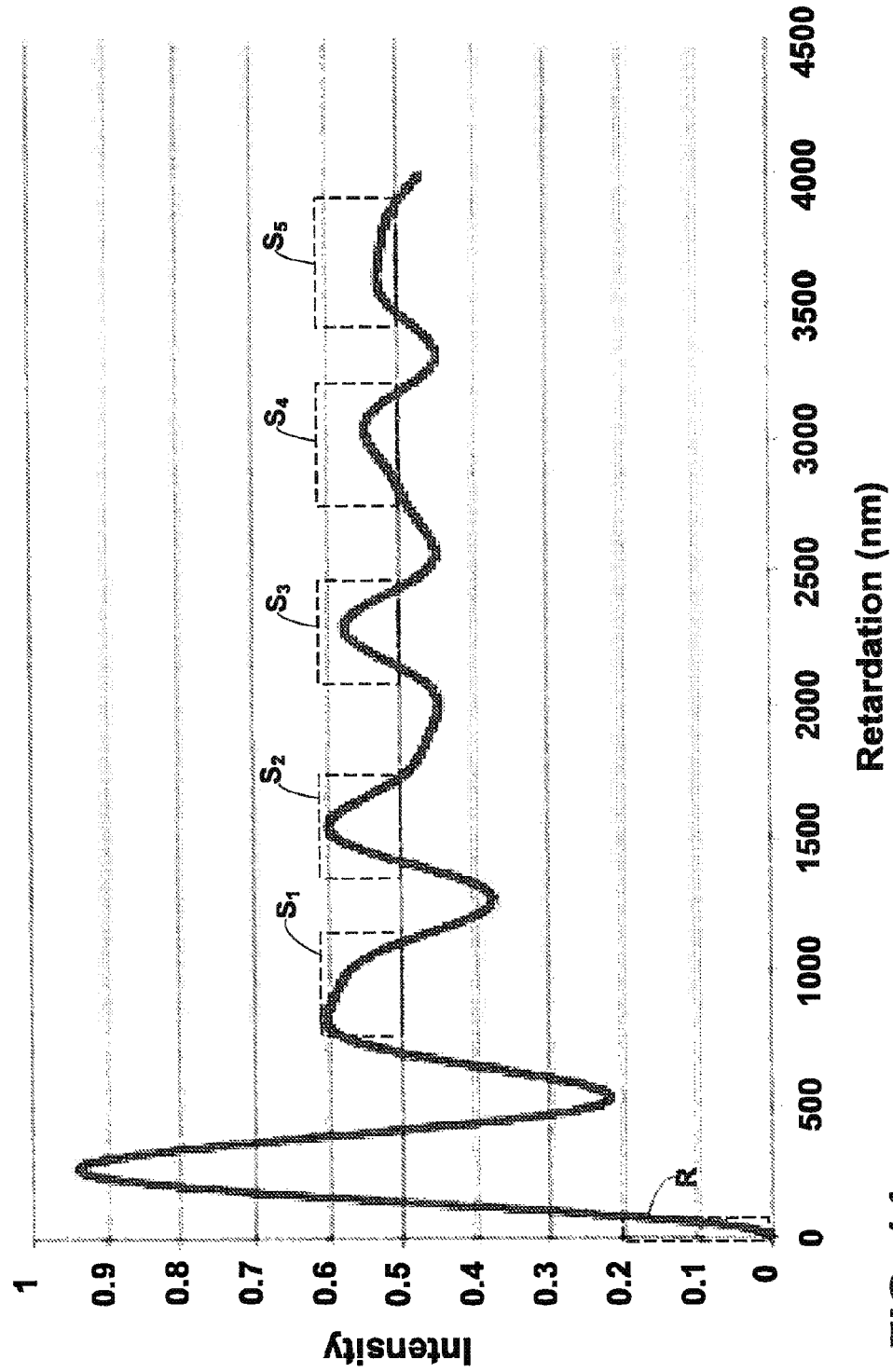
FIG. 14 illustrates a graph of retardation versus intensity as measured by a detector for the apparatus of FIG. 13 when operating in a first mode.
Figure 15:
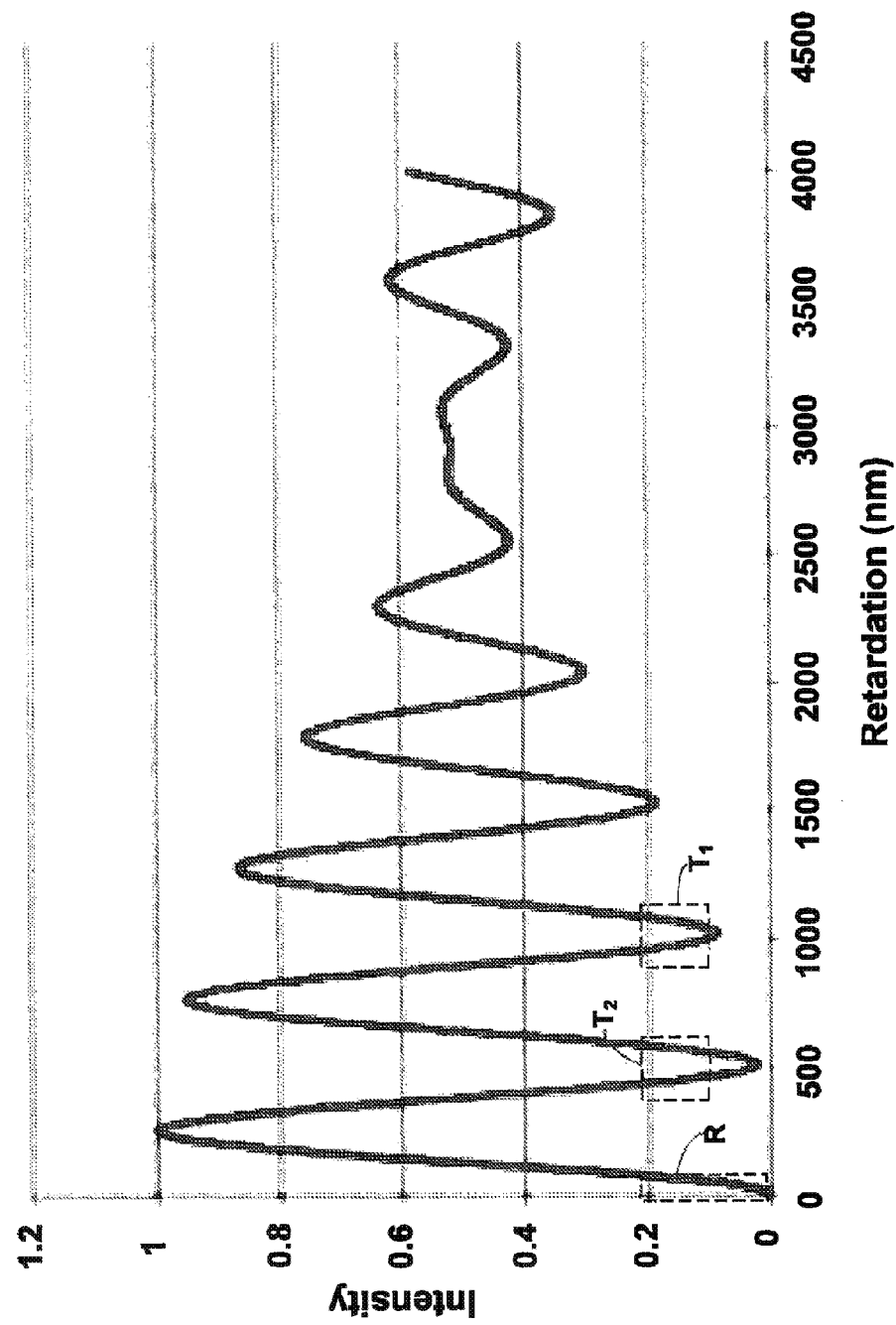
FIG. 15 illustrates a graph of retardation versus intensity as measured by a detector for the apparatus of FIG. 13 when operating in a second mode.
Figure 16:
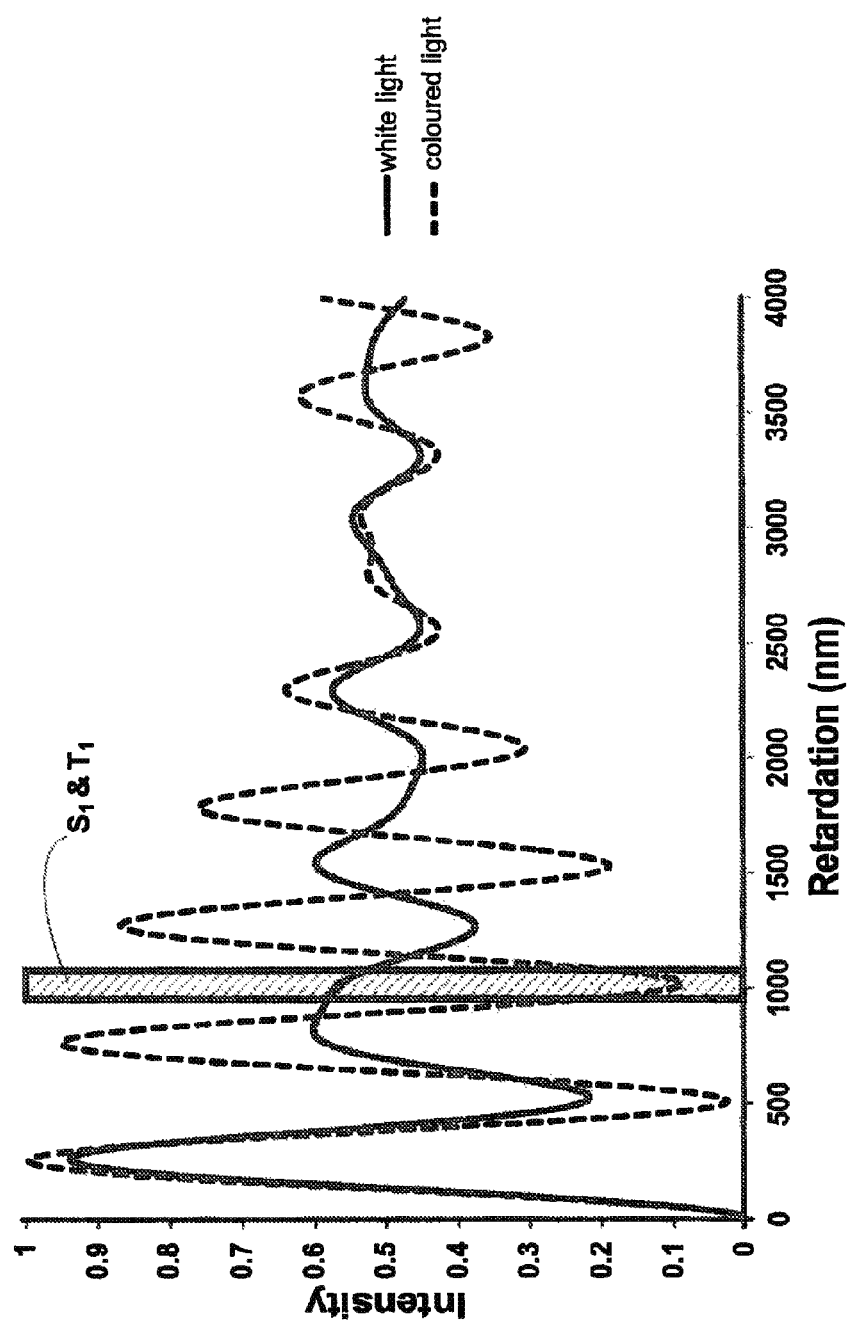
FIG. 16 illustrates a combined graph of the graphs of FIGS. 14 and 15.

FIGS. 1 to 3 schematically illustrate components of known apparatus for implementing different methods of observing birefringence;

FIGS. 4a to 4d schematically illustrate perspective, top-plan, side and end views of an authentication apparatus in accordance with one or more embodiments of the present invention;

FIG. 5 schematically illustrates a perspective view of the authentication apparatus of FIGS. 4a to 4d in an optional arrangement;

FIG. 6 schematically illustrates a perspective view of the authentication apparatus of FIGS. 4a to 4d in another optional arrangement;

FIGS. 7a and 7b schematically illustrate perspective views of another authentication apparatus in accordance with one or more embodiments of the present invention;

FIG. 8 schematically illustrates a perspective view of a further authentication apparatus in accordance with one or more embodiments of the present invention;

FIG. 9 schematically illustrates a perspective view of yet another authentication apparatus in accordance with one or more embodiments of the present invention;

FIG. 10 schematically illustrates a perspective view of yet another authentication apparatus in accordance with one or more embodiments of the present invention;

FIG. 11 illustrates a graph of birefringence versus percentage transmission for a 60 μm BOPP film; and FIG. 12 illustrates a Michel-Levy chart;

FIG. 13 schematically illustrates a perspective view of an optional arrangement of the apparatus illustrated in FIG. 10;

FIG. 14 illustrates a graph of retardation versus intensity as measured by a detector for the apparatus of FIG. 13 when operating in a first mode;

FIG. 15 illustrates a graph of retardation versus intensity as measured by a detector for the apparatus of FIG. 13 when operating in a second mode; and FIG. 16 illustrates a combined graph of the graphs of FIGS. 14 and 15.

FIGS. 4a to 4d illustrate an authentication apparatus 100 which comprises a birefringence measuring apparatus 102, a processor 104 and an alert system 106.

The authentication apparatus 100 is operative to measure birefringence characteristics of an item 108 (e.g. a banknote). In particular, the authentication apparatus 100 is operative to measure birefringence of a portion of the item 108 located in a measuring region of the authentication apparatus 100.

Processor 104 (optionally a microcontroller) is operative to control the birefringence measuring apparatus 102. An input of the birefringence measuring apparatus 102 is coupled to the processor 104 and is controllable by the processor 104. An output of the birefringence measuring apparatus 102 is coupled to the processor 104. The processor 104 is operative to determine whether or not the item 108 in the authentication apparatus is authentic based upon an output signal received from the birefringence measuring apparatus 102. An outcome of such determination is indicated (e.g. to an apparatus operator) via alert system 106. The alert system 106 is coupled to the processor 104 and is operative to output an indication of authenticity or otherwise based upon a signal received from said processor 104.

The birefringence measuring apparatus 102 comprises an emitter 110 (optionally an LED), a first polariser 112, a second polariser 114, and a detector 116 (optionally a photodiode). The polarisers 112, 114 are spaced apart and oriented so as to be substantially parallel. The region between the polarisers 112, 114 defines a measuring region.

The elements of the birefringence measuring apparatus 102 are arranged such that the emitter 110 and first polariser 112 are located on a first side of the measuring region of the birefringence measuring apparatus 102, and the first detector 116 and the second polariser 114 are located on a second side of the measuring region (i.e. opposite the first emitter 110 and first polariser 112).

Emitter 110 is operative to illuminate the first polariser 112 with electromagnetic radiation (denoted by arrow IL in the figure). This illuminating electromagnetic radiation IL is polarised by the first polariser 112 as it passes therethrough and continues as polarised illuminating electromagnetic radiation (denoted by arrow PIL in the figure) to irradiate a portion of the item 108 located in the measuring region. A portion of the polarised illuminating electromagnetic radiation which is transmitted through a portion of the item 108 (denoted by arrow TL) continues toward second polariser 114. This transmitted electromagnetic radiation TL is polarised by second polariser 114 as it passes therethrough, and continues as polarised transmitted electromagnetic radiation (denoted by arrows PTL1, PTL2, PTL3) towards detector 116. The detector 116 is located, oriented and operative to receive the polarised transmitted electromagnetic radiation PTL1, PTL2 or PTL3.

The measuring region generally defines a plane between the spaced polarisers 112, 114. The first polariser 112 is spaced from this first plane and is located in a second plane on a first "upstream" side of the measuring region. The second plane is substantially parallel to the first plane. Similarly, the second polariser 114 is spaced from the first plane and is located in a third plane on a second "downstream" side of the measuring region. It is located opposite the first polariser 112, and the third plane is substantially parallel to the first and second planes. The arrangement of transmission orientations of the first and second polarisers 112, 114 is such that they comprise crossed polarisers. That is, the first polariser 112 is arranged such that a transmission orientation thereof is about +45° to a transmission orientation of the portion of the item 108 located in the measuring region. The second polariser 114 is arranged such that a transmission orientation thereof is about −45° to the transmission orientation of the portion of the item 108 located in the measuring region. Alternatively, the transmission orientation of the first polariser 112 may be such that it is about −45° to a transmission orientation of the portion of the item 108 located in the measuring region and the transmission orientation of the second polariser 114 may be such that it is about +45° to the transmission orientation of the portion of the item 108 located in the measuring region.

Thus, in the illustrated arrangement, the illuminating electromagnetic radiation IL emitted by emitter 110 will be polarised by the first polariser 112, and will irradiate the portion of the item 108 located in the measuring region as polarised illuminating electromagnetic radiation PIL. This polarised illuminating electromagnetic radiation PIL passes through the item 108, and continues as transmitted electromagnetic radiation TL to the second polariser 114 (i.e. crossed polariser). The transmitted electromagnetic radiation TL passes through second polariser 114 and continues as polarised transmitted electromagnetic radiation PTL1, PTL2, or PTL3 for reception by the detector 116. The detector 116, responsive to detection of polarised transmitted electromagnetic radiation PTL1 or PTL2 or PTL3 incident thereon, outputs a signal proportional to the intensity of polarised transmitted electromagnetic radiation PTL1 or PTL2 or PTL3 respectively to the processor 104.

The detector 116 is mounted on a translation device (not shown). The translation device is controllable by the processor 104 to alter a position of the detector 116 relative to the second polariser 114. This can enable the detector 116 to measure polarised transmitted electromagnetic radiation transmitted from the second polariser 114 at different angles.

Such an arrangement is illustrated in FIGS. 4a to 4d using a convention where the detector is denoted using dotted lines (and the reference numeral 116') when positioned to receive polarised transmitted electromagnetic radiation transmitted from the second polariser 114 at a first angle θ (i.e. polarised transmitted electromagnetic radiation transmitted by said polariser 114 denoted by dotted arrow PTL1). The detector is denoted using dotted lines (and the reference numeral 116") when positioned to receive polarised transmitted electromagnetic radiation transmitted from the second polariser 114 at a second angle Φ (i.e. polarised transmitted electromagnetic radiation transmitted by said polariser 114 denoted by dotted arrow PTL2). The detector is denoted using solid lines (and the reference numeral 116) when positioned to receive polarised transmitted electromagnetic radiation transmitted from the second polariser 114 at a third angle (i.e. polarised transmitted electromagnetic radiation transmitted by said polariser 114 denoted by solid arrow PTL3).

In the illustrated arrangement, the detector 116 is operative to measure received polarised transmitted electromagnetic radiation transmitted from the second polariser 114 at three different angles, namely: at a first angle θ (optionally 45°) to the normal to the plane of the second polariser 114; at a second angle Φ (optionally 45°) to the normal to the plane of the second polariser 114 in both a horizontal and vertical direction: and at a third angle normal to the plane of the second polariser 114 (and consequently at a normal to the plane of the film in the item 108). Thus, the detector 116 will output three measurement signals to the processor 104.

The processor 104, upon receiving the three output measurement signals from the first detector 116, is operative to: compare a value of a first of the received signals with a first set of pre-defined values stored in a database (not shown); compare a value of a second of the received signals with a second set of pre-defined values stored in the database; and compare a value of a third of the received signals with a third set of pre-defined values stored in the database. These pre-defined values correspond to expected polarised transmitted electromagnetic radiation values when an authentic item (e.g. an authentic film) is located in the measuring region.

The processor 104, after conducting the comparison, is operative to instruct the alert system 106 to indicate that the film/item is authentic or non-authentic. If the result of the comparison is positive (i.e. the film is authentic), the processor is operative to send a signal to the alert system 106 containing an instruction to issue an indication that the film/item is authentic. Otherwise, the processor is operative to send a signal to the alert system 106 containing an instruction to issue an indication that the film/item is non-authentic.

The authentication apparatus 100 need not measure the polarised transmitted electromagnetic radiation at all three angles in order to determine authenticity of the item located therein. Indeed, in an optional arrangement, the authentication apparatus 100 may measure two angles only as part of an authentication exercise.

An item 108 comprising a film that is highly oriented will give rise to a high reading from the detector 116 when the polarised transmitted electromagnetic radiation transmitted from the second polariser (PTL3) is measured at the normal to the plane of the film (because a large amount of electromagnetic radiation will be transmitted, i.e. polarised transmitted electromagnetic radiation transmitted from the second polariser (PTL3) will be relatively high). However, a balanced film will give rise to a zero-value or low reading from the detector 116 when the polarised transmitted electromagnetic radiation transmitted from the second polariser (PTL3) is measured at the normal to the plane of the film because the behaviour of the electromagnetic radiation through the first and second crossed polarisers will be largely unaltered.

Cast films and bubble films (e.g. BOPP films) will produce a relatively low birefringence signal at detector 116 when the polarised transmitted electromagnetic radiation transmitted from the second polariser (PTL3) is measured at the normal to the plane of the film. On the other hand, when a stenter film is located in the measuring region, the detector 116, when measuring the polarised transmitted electromagnetic radiation transmitted from the second polariser (PTL3) at the normal to the plane of the film will, produce a high birefringence signal that will be different from the birefringence signals for cast and bubble films. This difference between the birefringence signal for a stenter film compared with the expected signal if the film is a bubble film is found by the processor 104 when it compares the output signal from the detector 116 with a predefined value indicative of an authentic film (i.e. a value representative of birefringence for a particular film type which is deemed to be genuine). The processor 104, after conducting the comparison, is operative to instruct the alert system 106 to indicate that the film/item is non-authentic.

The apparatus may be suitable, for example, in cases where genuine items comprise substrates formed by the bubble process and where, in general, counterfeit items comprise substrates formed by the stenter process. However, in instances where genuine items comprise substrates formed by the stenter process, further processing steps may be required in order to provide an indication regarding whether or not an item with a stenter-type film substrate is genuine or otherwise.

The differences in output signal from the detector 116 when the polarised transmitted electromagnetic radiation transmitted from the second polariser (PTL3) is measured at the normal to the plane of the film for cast or bubble films are relatively small. Therefore, it may be difficult for the authentication apparatus 100 to distinguish between these two types of films when relying solely upon a measurement of the polarised transmitted electromagnetic radiation transmitted from the second polariser at the normal to the plane of the film (i.e. PTL3). In this instance, or in an alternative instance where measurements are taken from non-normal angles, the authentication apparatus 100 may be operative to measure the polarised transmitted electromagnetic radiation transmitted from the second polariser 114 at one or both of the first θ and second angles Φ. Output signals from the detector 116 when located to receive polarised transmitted electromagnetic radiation transmitted from the second polariser 114 (PTL1, PTL2) at the first and/or second angles can be used by the processor 104 as further parameters (or alternative parameters) for a comparison process to determine the authenticity or otherwise of the film/item located in the measuring region.

The positioning of the detector 116 at positions so as to receive polarised transmitted electromagnetic radiation transmitted from the second polariser 114 at different angles can conveniently be described using planar geometry. A plane is defined as the surface that is normal to a vector of coordinates [x y z]. A plane that is normal to the vector (001) is defined as a (001) plane. Thus, in the arrangement described above and as illustrated in FIGS. 4a to 4d, when the detector 116 is located to measure polarised transmitted electromagnetic radiation transmitted from the second polariser at the normal to the plane of the film (i.e. (PTL3)), its position relative to the plane of the film (assuming the plane of the film is an x-y plane) can be defined by the geometric direction described by the vector (001). The detector 116 is effectively observing the x-y plane of the film (i.e. the (001) plane) along the z-axis (i.e. defined by vector (001)).

Similarly, for the situation when the detector 116 is located to measure polarised transmitted electromagnetic radiation transmitted from the second polariser at the first angle θ (i.e. (PTL1)), that first angle θ may be 45° to the normal to the plane of the second polariser 114. Using the planar geometry vector convention, the position of the detector 116 relative to the plane of the film can (in one instance) can be defined by the geometric direction described by the vector (110). Thus, detector 116 is observing the (110) plane of the film along a direction defined by vector (110).

For the situation when the detector 116 is located to measure polarised transmitted electromagnetic radiation transmitted from the second polariser at the second angle Φ (i.e. (PTL2)), that second angle Φ may be 45° to the normal to the plane of the second polariser 114 in both a horizontal and vertical direction. Using the planar geometry vector convention, the position of the detector 116 relative to the plane of the film can be defined by the geometric direction described by the vector (111). Thus, detector 116 is observing the (111) plane of the film along a direction defined by vector (111).

The measurements taken at the first θ and second angles Φ may be suitable for allowing the apparatus 100 to distinguish between bubble and cast films. Measurements taken of such films at the normal to the plane of such films may be relatively similar and so the further measurements at the first and second angles, when used in the comparison by the processor, can be used to distinguish between the two types.

In an optional arrangement, the authentication apparatus 100 may comprise a path along which an item may be conveyed. The measuring region forms part of this path. Thus, in this particular arrangement, the item may be conveyed along the path from one side of the authentication apparatus 100 to the other and, during its transit, pass through the measuring region. That is, in this optional arrangement, the item to be authenticated may be moved relative to the authentication apparatus 100 or vice versa. In another optional arrangement, authentication measurement may take place when an item is static. That is, the item may be introduced to an item location region (of which the measuring region forms part) of the authentication apparatus 100, where the item is held until an authentication measurement has taken place.

This apparatus 100 may be implemented in, for example, a banknote authentication system.

The operation of the authentication apparatus 100 illustrated in FIGS. 4a to 4d may be summarised as follows. Birefringence measurement is performed on an item/film located in the measuring region. At least one birefringence measurement is performed with the detector 116 at least one non-normal angle relative to the plane of the film. The processor compares a value of the signal arising from the birefringence measurement with a value corresponding to an authentic film. If a measured value matches the value corresponding to an authentic film (or lies within a suitable range of values deemed to be authentic), then the processor is operative to instruct the alert system to provide an indication that the film is authentic. However, if one of the measured values (optionally two of the measured values, further optionally three of the measured values) does not match the value (or values) corresponding to an authentic film (or lie outside a suitable range of values deemed to be authentic), then the processor is operative to instruct the alert system to provide an indication that the film is not authentic.

FIG. 5 illustrates an optional arrangement of the authentication apparatus 100 illustrated in FIGS. 4a to 4d and as described above.

The arrangement is similar to that illustrated in FIGS. 4a to 4d and as described above except that the movable detector 116 is replaced by two fixed detectors 116a, 116b. First fixed detector 116a is located to receive polarised transmitted electromagnetic radiation transmitted from the second polariser 114 (denoted by arrow PTL1) at a first angle θ. The second fixed detector 116b is located to receive polarised transmitted electromagnetic radiation transmitted from the second polariser 114 (denoted by arrow PTL2) at a second angle.

In this arrangement, the first and second fixed detectors 116a, 116b may measure the respective portions (i.e. PTL1, PTL2) of polarised transmitted electromagnetic radiation transmitted from the second polariser 114 simultaneously.

The processor 104, upon receiving an output measurement signal from the first fixed detector 116a and the second fixed detector 116b, is operative to: compare a value of a signal received from the first fixed detector 116a with a first set of pre-defined values stored in a database (not shown); and compare a value of a signal received from the second fixed detector 116b with a second set of pre-defined values stored in the database. These pre-defined values correspond to expected polarised transmitted electromagnetic radiation values when an authentic item (e.g. an authentic film) is located in the measuring region.

The processor 104, after conducting the comparison, is operative to instruct the alert system 106 to indicate that the film/item is authentic or non-authentic. If the result of the comparison is positive (i.e. the film is authentic), the processor is operative to send a signal to the alert system 106 containing an instruction to issue an indication that the film/item is authentic. Otherwise, the processor is operative to send a signal to the alert system 106 containing an instruction to issue an indication that the film/item is non-authentic.

FIG. 6 illustrates yet another optional arrangement of the authentication apparatus 100 illustrated in FIGS. 4a to 4d and as described above.

The arrangement is similar to that illustrated in FIG. 5 except that three fixed detectors (116a, 116b, 116c) are employed instead of two. First fixed detector 116a is located to receive polarised transmitted electromagnetic radiation transmitted from the second polariser 114 (denoted by arrow PTL1) at a first angle θ. A second fixed detector 116b is located to receive polarised transmitted electromagnetic radiation transmitted from the second polariser 114 (denoted by arrow PTL2) at a second angle Φ. A third fixed detector 116c is located to receive polarised transmitted electromagnetic radiation transmitted from the second polariser 114 (denoted by arrow PTL3) at a third angle.

In this arrangement, the first, second and third fixed detectors 116a, 116b, 116c may measure the respective portions (i.e. PTL1, PTL2, PTL3) of polarised transmitted electromagnetic radiation transmitted from the second polariser 114 simultaneously.

The processor 104, upon receiving an output measurement signal from the first fixed detector 116a, the second fixed detector 116b, and the third fixed detector 116c is operative to: compare a value of a signal received from the first fixed detector 116a with a first set of pre-defined values stored in a database (not shown); compare a value of a signal received from the second fixed detector 116b with a second set of pre-defined values stored in the database; and compare a value of a signal received from the third fixed detector 116c with a third set of pre-defined values stored in the database. As described previously, these pre-defined values correspond to expected polarised transmitted electromagnetic radiation values when an authentic item (e.g. an authentic film) is located in the measuring region.

As described above, the processor 104, after conducting the comparison, is operative to instruct the alert system 106 to indicate that the film/item is authentic or non-authentic. If the result of the comparison is positive (i.e. the film is authentic), the processor is operative to send a signal to the alert system 106 containing an instruction to issue an indication that the film/item is authentic. Otherwise, the processor is operative to send a signal to the alert system 106 containing an instruction to issue an indication that the film/item is non-authentic.

In another optional arrangement, the authentication apparatus 100 may employ an arrangement of both fixed and moveable detectors and/or may be arranged to measure polarised transmitted electromagnetic radiation transmitted from the second polariser 114 at four or more angles.

FIGS. 7a and 7b illustrate another authentication apparatus in accordance with one or more embodiments of the present invention.

Features similar to those illustrated in FIG. 4a to 4d, 5 or 6 are also illustrated in FIGS. 7a and 7b. In FIGS. 7a and 7b, the features common with those of FIG. 4a to 4d, 5 or 6 are designated with reference numerals of the type 2XX rather than 1XX. Thus, in FIGS. 7a and 7b, the authentication apparatus is denoted by reference number 200 (rather than 100), the birefringence measuring apparatus, by reference number 202 (rather than 102) and so on.

The authentication apparatus 200 illustrated in FIGS. 7a and 7b differs from the authentication apparatus 100 previously described (and as illustrated in FIG. 4a to 4d, 5 or 6) in that second polariser 214 is rotatable between a polarising orientation (as illustrated in FIG. 7a) and a non-polarising orientation, or normal transmission orientation (as illustrated in FIG. 7b). When oriented in the polarising orientation, second polariser 214 acts in the same manner as the second polariser 114 as previously described. That is, the transmission orientation of the second polariser 214 is perpendicular to that of the first polariser 212 such that the first and second polarisers 212, 214 comprise crossed polarisers. Therefore, and as with the arrangement of transmission orientations of the first and second polarisers 112, 114 previously described, the first polariser 212 is arranged such that a transmission orientation thereof is about +45° to a transmission orientation of the portion of the item 208 located in the measuring region. The second polariser 214 (in the polarising orientation) is arranged such that a transmission orientation thereof is about −45° to the transmission orientation of the portion of the item 208 located in the measuring region. Alternatively, the transmission orientation of the first polariser 212 may be such that it is about −45° to a transmission orientation of the portion of the item 208 located in the measuring region and the transmission orientation of the second polariser 214 may be such that it is about +45° to the transmission orientation of the portion of the item 208 located in the measuring region.

When oriented in the non-polarising orientation, the transmission orientation of the second polariser 214 is the same as that of the first polariser 212 (i.e. it is parallel with the transmission orientation of the first polariser 212). In this instance, the first and second polarisers 212, 214 are arranged such that transmission orientations thereof are about +45° to a transmission orientation of the portion of the item 208 located in the measuring region. Alternatively, the transmission orientations of the first and second polarisers 212, 214 may be such that they are about −45° to a transmission orientation of the portion of the item 208 located in the measuring region.

The authentication apparatus 200 includes an actuator (not shown) which is operative to effect rotation of the second polariser 214 from the polarising orientation to the non-polarising orientation, and vice versa. The processor 204 is operative to control the actuator.

In operation, the detector 216 is operative to measure received polarised transmitted electromagnetic radiation transmitted from the second polariser 214 (denoted by arrow PTL in FIG. 7a) when the second polariser 214 is oriented in the polarising orientation. A first measurement signal is communicated to the processor 204.

The detector 216 is further operative to measure received transmitted electromagnetic radiation transmitted from the second polariser 214 (denoted by arrow TL in FIG. 7b) when the second polariser is oriented in the non-polarising orientation. A second measurement signal is communicated to the processor 204.

The processor 204, upon receiving the first and second measurement signals from the detector 216, is operative to: compare a value of a received first measurement signal with a first set of pre-defined values stored in a database (not shown); and/or compare a value of a received second measurement signal with a second set of pre-defined values stored in the database. The first set of pre-defined values corresponds to expected polarised transmitted electromagnetic radiation values when an authentic item (e.g. an authentic film) is located in the measuring region. The second set of pre-defined values corresponds to expected direct transmission electromagnetic radiation values when an authentic item/film is located in the measuring region (e.g. a value indicative of an intensity of electromagnetic radiation transmitted by an authentic item/film directly).

In an optional arrangement, the processor 204 may be operative to subtract the value of the received second measurement signal from a pre-defined value indicative of there being no item/film located in the measuring region. The processor 204 is then operative to compare the resultant value of the subtraction with a different second set of pre-defined values which correspond to expected transmitted electromagnetic radiation values (birefringence values) when an authentic item/film is located in the measuring region.

In this optional arrangement, the intensity of electromagnetic radiation transmitted by the item/film 208 to the detector 216 with the second polariser 214 in the non-polarising orientation has a value $I_{NP}$. If no item/film 208 is present in the measuring region, then the illuminating radiation simply passes through air in the measuring region, and the intensity of the electromagnetic radiation received at the detector 216 with the polariser 214 in the non-polarising orientation has a value $I_{AIR}$. To obtain the resultant value ($I_{RV}$) described above, the intensity value $I_{NP}$ is subtracted from the intensity value $I_{AIR}$. Thus, $I_{AIR}-I_{NP}=I_{RV}$. Resultant value $I_{RV}$ is effectively a measure of the birefringence of the film. Comparison of this resultant value $I_{RV}$ with the different second set of pre-defined values by the processor 204 allows the processor 204 to make an authentication determination.

As has been described previously, in an arrangement comprising two crossed polarisers with a birefringent material located therebetween, birefringence results from the interference caused by the recombination of the ordinary and extraordinary rays upon transmission by the second crossed polariser. The birefringent electromagnetic radiation is constructed as one polarisation and passes through the second polariser whilst the remainder is constructed in the opposite polarisation and is reflected or absorbed by the second polariser. The non-transmitted electromagnetic radiation can be transmitted if the second polariser is rotated so that it is parallel to the first one instead of crossed. This effect is employed in the above described arrangement.

Films, or items comprising films, with a relatively low level of birefringence cannot be differentiated from air and, in the case of crossed polarisers, may not be visible next to a printed surround. The previously described and later described arrangements rely upon the phenomena of birefringence effectively redirecting electromagnetic radiation and the use of crossed polarisers to view that electromagnetic radiation to allow for one part of the redirected radiation to be observed. The other part (i.e. the "non-transmitted" part referred to above) can be seen when the polarisers are parallel. The behaviour of an apparatus employing parallel polarisers is that electromagnetic radiation of high intensity is transmitted, and the intensity of this electromagnetic radiation will decrease with birefringence (e.g. when a birefringent film is introduced into the apparatus between the polarisers). In this parallel polariser instance, an empty apparatus will cause electromagnetic radiation of high intensity to be received at the detector whereas a film located in the measuring region of the apparatus will cause electromagnetic radiation of a lower intensity to be received at the detector. The difference between a measurement of the electromagnetic radiation of high intensity (apparatus empty) and the electromagnetic radiation of slightly lower intensity (film present) provides a measure of the birefringence of the film.

Therefore, the authentication apparatus 200 described above, and as illustrated in FIGS. 7*a* and 7*b*, may be suitable for determining authenticity of films which exhibit relatively low levels of birefringence. Indeed, since highly oriented films such as, for example, BOPP film, have a relatively low level of birefringence (possibly zero in some instances), any "measure" of this characteristic using an apparatus in which the polarisers are in a crossed configuration may give a result which might be indistinguishable from background noise. A measurement taken using an apparatus where the polarisers are not in a crossed configuration may allow a measurement representative of "inverse" birefringence to be taken (i.e. intensity of electromagnetic radiation received when the apparatus is empty ($I_{AIR}$) minus intensity of electromagnetic radiation received when a film is located in the measuring region of the apparatus ($I_{NP}$) equals $I_{RV}$, and $I_{RV}$ is proportional to the "inverse" birefringence of the film, i.e. a film transmissivity)).

In the arrangement above (and the optional arrangement), the processor 204, after conducting the comparison, is operative to instruct the alert system 206 to indicate that the film/item is authentic or non-authentic. If the result of the comparison is positive (i.e. the film is authentic), the processor is operative to send a signal to the alert system 206 containing an instruction to issue an indication that the film/item is authentic. Otherwise, the processor is operative to send a signal to the alert system 206 containing an instruction to issue an indication that the film/item is non-authentic.

This arrangement may also be suitable for an apparatus operative to determine the authenticity of banknotes having a polymer film substrate and in which authenticity measurements are conducted on a "window" region of the banknote, i.e. a region of the banknote where the film substrate is exposed (e.g. there is no print overlying the region or no overt security features overlying the region). As will be appreciated, banknotes become worn over time and one aspect of wear of a banknote may manifest itself as damage to the window region of the banknote. Such damage may comprise, for example, scratches to the window surface and/or greasy substances being transferred to the window surface, both of which may cause the window to have a hazy appearance. These forms of "damage" can effectively physically block (or partially block) the transmission of light through the window region of the banknote. This may affect measurements taken during an authentication process.

In the arrangement described above in relation to FIGS. 7*a* and 7*b*, physical blocking of the window region of a banknote (e.g. through damage) is observable as an effective decrease in birefringence in the crossed polariser mode of operation. However, physical blocking of the window region of the banknote is observable as an effective increase in birefringence in the non-crossed polarised mode of operation. In both cases, the physical blocking does not alter the birefringence of the film substrate itself, but rather affects the measurements taken by the detector and is thus perceived to be a different birefringence than is, in fact, the case.

A more accurate measure of the birefringence of a damaged/hazy film may be obtained by performing calculations using the intensity values obtained in the crossed polariser mode of operation (i.e. the polarising mode) and the non-crossed polariser mode of operation (i.e. the non-polarising mode). As described above, the intensity of electromagnetic radiation received at the detector when the second polariser is in the non-polarising orientation (i.e. the non-crossed polariser mode of operation) is denoted by $I_{NP}$. Intensity of electromagnetic radiation received at the detector when the second polariser is in the polarising orientation (i.e. the crossed polariser mode of operation) is denoted by $I_P$. To determine the intensity which may be expected if the window region of the film was undamaged (or not obscured), and thus a measure of the birefringence of the film, a difference between the two intensity values may be obtained and this difference value is then halved. The resultant value is either subtracted from $I_{NP}$ or added to $I_P$ to obtain a more accurate measure of the birefringence of the film ($I_{UNDAMAGED}$). i.e.

$$(I_{NP}-I_P)/2+I_P=I_{UNDAMAGED}$$

OR $$I_{NP}-(I_{NP}-I_P)/2=I_{UNDAMAGED}$$

This birefringence representative value (i.e. $I_{UNDAMAGED}$) can be compared to the pre-defined value by the processor 204 in the authenticity determination.

FIG. 8 illustrates another authentication apparatus in accordance with one or more embodiments of the present invention.

Again, features similar to those illustrated in FIG. 4a to 4d, 5, 6, 7a or 7b are also illustrated in FIG. 8. In FIG. 8, the features common with those of FIG. 4a to 4d, 5, 6, 7a or 7b are designated with reference numerals of the type 3XX rather than 1XX or 2XX. Thus, in FIG. 8, the authentication apparatus is denoted by reference number 300 (rather than 100 or 200), the birefringence measuring apparatus, by reference number 302 (rather than 102 or 202) and so on.

The authentication apparatus 300 illustrated in FIG. 8 differs from the authentication apparatus 100 previously described (and as illustrated in FIGS. 4a to 4d) in that detector 116 is replaced by (or supplemented by, in a non-illustrated optional arrangement) an imaging array 320 (e.g. a photosensitive array).

As with the arrangement of transmission orientations of the first and second polarisers 112, 114 previously described, the first polariser 312 is arranged such that a transmission orientation thereof is about +45° to a transmission orientation of the portion of the item 308 located in the measuring region. The second polariser 314 (in the polarising orientation) is arranged such that a transmission orientation thereof is about −45° to the transmission orientation of the portion of the item 308 located in the measuring region. Alternatively, the transmission orientation of the first polariser 312 may be such that it is about −45° to a transmission orientation of the portion of the item 308 located in the measuring region and the transmission orientation of the second polariser 314 may be such that it is about +45° to the transmission orientation of the portion of the item 308 located in the measuring region.

The imaging array 320 is operative to image at least a portion of said film as observed from the location of the imaging array 320 through second polariser 314. That is, imaging array 320 is located to receive polarised transmitted electromagnetic radiation transmitted from the second polariser 314 (denoted by arrow PTL in FIG. 8). The imaging array 320 (alone or in conjunction with processor 304) is operative to compile an image of a particular portion or area of a film of the item 308 from the polarised transmitted electromagnetic radiation transmitted from the second polariser 314 and received by the imaging array 320.

The processor 304 is operative to compare a data-set corresponding to a compiled image with a data-set of pre-defined values stored in a database (not shown). The data-set of pre-defined values corresponds to an expected image which would be observed when an authentic item (e.g. an authentic film) is located in the measuring region.

The processor 304, after conducting the comparison, is operative to instruct the alert system 306 to indicate that the film/item is authentic or non-authentic. If the result of the comparison is positive, i.e. the compiled image data-set matches the data-set of pre-defined values corresponding to an expected image of an authentic film/item, then the film is deemed to be authentic and the processor is operative to send a signal to the alert system 306 containing an instruction to issue an indication that the film/item is authentic. Otherwise, the processor is operative to send a signal to the alert system 306 containing an instruction to issue an indication that the film/item is non-authentic.

An authentication method implemented by the apparatus 300 of this arrangement may be suitable for implementing area observations of a film/item rather than spot observations as implemented by the other arrangements described above. Employing this "area observation" technique may allow for authentication of a film based upon an inherent birefringent pattern of the film which would be observable using the apparatus 300 of FIG. 8. Thus, a birefringent pattern (if present) will be captured in the compiled image, and this observed birefringent pattern can be compared to a pre-defined image (i.e. a birefringent pattern) which would be expected to be observed if an authentic film is present in the apparatus 300.

In an optional arrangement of the one or more embodiments described above, and as illustrated in FIG. 8, the emitter 310 may comprise a white-light source (e.g. a light-box), and/or the imaging array 320 may comprise a CCD camera. In another optional arrangement, the imaging array 320 may comprise a flat-bed scanner.

FIG. 9 illustrates another authentication apparatus in accordance with one or more embodiments of the present invention.

Again, features similar to those illustrated in previous figures are also illustrated in FIG. 9. In FIG. 9, the features common with those of previous figures are designated with reference numerals of the type 4XX rather than 1XX, 2XX or 3XX. Thus, in FIG. 9, the authentication apparatus is denoted by reference number 400 (rather than 100, 200 or 300), the birefringence measuring apparatus, by reference number 402 (rather than 102, 202 or 302) and so on.

The authentication apparatus 400 illustrated in FIG. 9 differs from those previously described (and as illustrated in FIGS. 4a to 4d, 5, 6) in that there is a single fixed detector 414 and in that it further comprises an optical response modifier 418.

The optical response modifier 418 is located (as are the first and second crossed polarisers 412, 414 and item 408) in a beam path of electromagnetic radiation between emitter 410 and detector 416.

The optical response modifier 418 is operative to modify an observable optical response of an item 408 located in the measuring region. A modification effect of the optical response modifier 418 is to modify an observed birefringence characteristic of the item 408 located in the measuring region. The optical response modifier 418 is provided to effectively introduce an offset of a predetermined amount to a value representative of intensity of polarised transmitted electromagnetic radiation as received at, and as measured by, the detector 416.

The optical response modifier 418 optionally comprises a material suitable to act as a half-wave or quarter-wave retardation plate. The optical response modifier 418 (e.g. a birefringent material) controls the response by providing additive or subtractive retardation which can be further altered by rotating the optical response modifier 418 with respect to rotational alignment of the item 408. The degree of alteration of retardation can be calculated using the following:

$$\Delta r = l \Delta n \cos \qquad (20)$$

where Δr is the change in retardation, Δn is the birefringence of the optical response modifier 418, l is the thickness of the optical response modifier 418 and θ is the rotational angle with respect to the item 408 measurement angle.

In operation therefore, transmitted electromagnetic radiation TL transmitted by said item 408 is polarised by second polariser 414 as it passes through the second polariser 414, and a portion of the transmitted electromagnetic radiation TL transmitted by said item 408 continues as polarised transmitted electromagnetic radiation (denoted by arrow PTL) towards detector 416. Before reaching detector 416, the polarised transmitted electromagnetic radiation PTL is incident upon optical response modifier 418. A portion of the incident polarised transmitted electromagnetic radiation PTL is not transmitted (e.g. reflected or absorbed) and a remaining portion is transmitted by the optical response modifier 418. This remaining portion (hereinafter "optically modified transmitted radiation" OMTL) continues to the detector 416 and is received thereat.

The detector 416, responsive to detection of optically modified transmitted radiation OMTL incident thereon, outputs a signal proportional to the intensity of optically modified transmitted radiation OMTL to the processor 404.

The processor 404, upon receiving the output measurement signal from the detector 416, is operative to: compare a value of the received signal with a set of pre-defined values stored in a database (not shown). These pre-defined values correspond to expected optically modified transmitted radiation OMTL values when an authentic item (e.g. an authentic film) is located in the measuring region.

The processor 404, after conducting the comparison, is operative to instruct the alert system 406 to indicate that the film/item is authentic or non-authentic. If the result of the comparison is positive (i.e. the film is authentic), the processor is operative to send a signal to the alert system 406 containing an instruction to issue an indication that the film/item is authentic. Otherwise, the processor is operative to send a signal to the alert system 406 containing an instruction to issue an indication that the film/item is non-authentic.

In prior art systems, birefringence is measured using equipment with a white-light emitter and then integrating (essentially averaging) the intensity of light that is received at the detector. That is, measurements are integrated across a white spectrum. This has meant that measurements taken for stenter films could be quite similar to measurements taken for BOPP bubble process films where the manufacturing process of those films was poorly controlled.

Measurement of birefringence has been standardised using a 0 to 1 scale, where a value of 0 represents no birefringence (i.e. a pair of crossed polarisers with no item present). A value of 1 represents birefringence when an item having "half-wave" properties (around 275 nm retardation) is present. In the standardised (i.e. 0 to 1) birefringence measurement scale used with previous measuring systems, a BOPP bubble process film would usually give rise to a measurement reading of about 0.3 in the standardised birefringence measurement scale. However, measurement readings of about 0.4 to about 0.6 in the standardised birefringence measurement scale could commonly be seen for stenter films.

In an optional arrangement, the optical response modifier 418 may be controllably rotatable by the processor 404 and an actuator (not shown) to alter an orientation of x and y birefringent axes of the optical response modifier 418.

Since birefringence is additive, it is possible to change the zero point of the standardised birefringence measurement scale by either adding positive birefringence or subtracting negative birefringence. Thus, two films with the same birefringence will add together to produce twice as much retardation (and consequently twice as much birefringence). The same two films, when positioned at 90° with respect to each other's orientation will effectively cancel one another out.

If an optical response modifier 418 (e.g. a film) having a 0.3 monochromatic birefringence in the opposite axis to that of the item which the equipment is to measure is provided, then a measurement value of optically modified transmitted radiation OMTL received at detector 416 will be 0.3 when there is no item in the measuring region. Placing samples with increasing retardation in the opposite axis will reduce this value until the sample (i.e. inserted item) birefringence is 0.3, when a measurement value of optically modified transmitted radiation OMTL received at detector 416 will be 0. Further increasing retardation in the opposite axis will increase the measurement value of optically modified transmitted radiation OMTL received at detector 416. Using this technique means that birefringence of 0 to 0.6 effectively becomes halved to 0.3.

A result of employing the above technique for white-light systems is that the gap is widened between detector measurement values for BOPP bubble process films at a high end of expected values for films of this type and detector measurement values for stenter films at a low end of expected values for films of this type.

The arrangement of FIG. 9 as described above may be suitable for assisting an ability to distinguish between stenter films having birefringence values in a range similar to those of BOPP bubble process films and BOPP bubble process films themselves. Thus, the apparatus may be suitable to identify genuine bubble process films, genuine non-bubble process films (e.g. authentic films made using a stenter process) or non-genuine non-bubble process films.

FIG. 10 illustrates another authentication apparatus in accordance with one or more embodiments of the present invention.

Again, features similar to those illustrated in previous figures are also illustrated in FIG. 10. In FIG. 10, the features common with those of previous figures are designated with reference numerals of the type 5XX rather than 1XX, 2XX, 3XX or 4XX. Thus, in FIG. 10, the authentication apparatus is denoted by reference number 500 (rather than 100, 200, 300 or 400), the birefringence measuring apparatus, by reference number 502 (rather than 102, 202, 302 or 402) and so on.

Before describing the authentication apparatus 500 of FIG. 10 in more detail, a birefringence measuring system as disclosed in WO 2009/133390 will be discussed as background technical information.

The system disclosed in WO 2009/133390 comprises an emitter→first polariser→second (crossed) polariser→detector system in which a film to be authenticated is positioned between the first and second polarisers.

The emitter of that system is operative to emit white-light. This white light which passes through the system comprises electromagnetic radiation not just of one wavelength, but of a whole range of wavelengths. Each wavelength in that range will interfere at the second polariser differently according to the relationship between it and its wavelength. Equation (3) can be used to calculate phase difference, p, which describes the relationship between wavelength, λ, and retardation:

$$p = \frac{2\pi}{\lambda} r = \frac{2\pi d(n_x - n_y)}{\lambda} \quad (3)$$

The amplitude, A, of a waveform formed by the interference of two waves with phase difference, p, can be calculated by using equation (4):

$$A = \sin\left(\frac{\pi + p}{2}\right) = \sin\left(\frac{\pi}{2} + \frac{\pi d(n_x - n_y)}{\lambda}\right) \quad (4)$$

For any ray of transmitted light, the intensity, I, can be calculated using equation (5):

$$I = 1 - A^2 = 1 - \left[\sin\left(\frac{\pi}{2} + \frac{\pi d(n_x - n_y)}{\lambda}\right)\right]^2 \quad (5)$$

Equation (5) allows the intensity of a wave at a particular wavelength to be calculated and can be used to build up spectra that show what the transmitted light will look like. However, it is the overall intensity of transmitted light, T, across a range that is to be measured and so this equation (5) has to be modified to equation (6) as follows:

$$T = \int_{\lambda min}^{\lambda max} I d\lambda = \int_{\lambda min}^{\lambda max} 1 - \left[\sin\left(\frac{\pi}{2} + \frac{\pi d(n_x - n_y)}{\lambda}\right)\right]^2 d\lambda \quad (6)$$

FIG. 11 shows the results of equation (6) as calculated for a 60 μm film over a range of 0 to 0.05 birefringence. As indicated previously, FIG. 11 shows the transmitted intensity of a film versus the level of birefringence. As can be seen, a peak is reached, followed by oscillating intensity drops and rises. FIG. 11 shows what an integrating detector would see; a film with a birefringence several times that which is possible for a film produced by the bubble process would have transmission values of as little as 30% on this scale, e.g. the region denoted by the box A (which is modelled, so the intensities may not be precise). As may be appreciated, these transmission values are similar to those at the upper end of the range of transmission values for a film produced by the bubble process (denoted by box B).

Birefringence is typically identified by reading from a Michel-Levy Chart, (illustrated herein in black and white only at FIG. 12). The bottom x-axis is the retardation (nm) and is divided into different orders depending on its behaviour. The first half of the first order (0-300 nm) is composed of a transition from a black to a white colour representing zero transmitting to a broad band of white light. This first order corresponds to the first peak in the graph illustrated in FIG. 11 (0-0.004). It should be noted that the intensity drops after the first half of the first order to a value of apparently 30% of the maximum. This corresponds with the end of a first order and can be measured in practice by using a full wave film. The measured value differs from the calculated one, being closer to 50% of the maximum, possibly due to simplifications in the model defined by the above equations and variations in real life equipment.

A white-light single-detector integrating system of the type disclosed in WO 2009/133390 effects a measurement at the detector end of the system which effectively is an integration of the transmission of all the light from a white light source into a single value. Because of this, it cannot resolve the colour changes found at retardations higher than the first order (see a full-colour version of the Michel-Levy chart illustrated at FIG. 12 for more detail). Therefore, some information is lost in measurements taken by a system of this type.

To illustrate further, reference is made again to FIG. 11. The transmission levels displayed in FIG. 11 can be mapped to the Michel-Levy chart illustrated in FIG. 12. The first cycle illustrated in FIG. 11 corresponds to the black to white transition of the first order of the Michel-Levy chart. The middle cycles illustrated in FIG. 11 correspond to colour bands (shown in black and white only in FIG. 12) on the higher orders of the Michel-Levy chart illustrated in FIG. 12. If a full-colour Michel-Levy chart is referred to, it can be seen that at the higher orders, colours are transmitted.

If the Michel Levy chart is taken and converted to a grey-scale, and then an intensity line taken across it, the resultant profile will be of approximately the same shape as that illustrated in FIG. 11.

It can be seen from FIG. 11 that a film with birefringence at 0.01 on this graph (denoted by point P) has about the same integrated transmission value as one at 0.002 (denoted by point Q) and yet (as can be seen by cross-reference to the Michel-Levy chart of FIG. 12) has five times the retardation.

A relationship between bubble film and stenter film is even more extreme. A 60 μm stenter film will have retardation values of between 800 and 1200 whereas the retardation value for bubble films will be less than about 200. However, converting these values to the graph of FIG. 11 gives transmissions that are approximately similar around 40% (retardation of 200 nm (Michel-Levy chart) corresponds to about 0.002-0.003 birefringence in FIG. 11; a retardation of 800-1000 nm corresponds to about 0.015-0.025 birefringence in FIG. 11).

So, this measurement technique returns similar values representative of birefringence for quite different films. The reasons for the transmission levels are quite different. The bubble film will have a near flat spectrum that will appear white to an observer's eye and the stenter film will transmit a specific colour that will be a result of a loss of part of the visible spectrum. This loss of part of the visible spectrum is what decreases the integrated intensity.

A measurement that allows for wavelength differentiation will expose this difference. The arrangement of FIG. 10 is operative to employ such a technique to try to avoid this loss of information referred to above. Further, the arrangement of FIG. 10 is designed to accommodate the colour information which may be transmitted (i.e. corresponding to the higher orders of the Michel-Levy chart). To do this, the arrangement of FIG. 10 may employ a 1 to 20 scale describing higher levels of birefringence to compliment the 0 to 1 scale referred to above. Such a scale may be employed by the processor when the processor operates to implement a process (described in more detail later) for converting a spectrum into a single value. The process, in general, allows wavelength information (essentially "colour" information) to be retained in any measurement and effectively adds a variance of a set of measured intensity values to the values themselves.

"Coloured" measurement, which may be implementable by the process in the processor 504 may reduce the sensitivity of the system to misaligned samples. For example a highly birefringent stenter film will transmit light in the red portion of the visible electromagnetic spectrum. That is, a detector would receive electromagnetic radiation at wavelengths corresponding to the red-portion of the visible electromagnetic spectrum. The stenter film will still transmit red light as it is rotated, but the measured intensity will decrease as the film is rotated. A white-light single-detector integrating system would interpret this decrease in intensity as the film is rotated as a decrease in birefringence. A colour measurement system shows that this is not the case. The birefringence/retardation remains the same as the film is rotated but the amount of retarded light that is transmitted decreases. This is due to two separate effects. For a film that retards to the first order (refer to a full-colour Michel-Levy chart), where the transmission is actually black→grey→white this is not obvious, for a film that transmits red light: if the degree of retardation were changing, then the observed colour would change. However, it does not, and the intensity of the observed red colour would simply decrease. A colour measurement system would register an overall decrease in intensity but a consistent spectral shape.

Using the authentication apparatus of FIG. 10, a "red" 1000 nm retarding film (i.e. a film that transmits red light) which has been inserted in the measuring region so as to be misaligned would still be detectable as non-bubble film (i.e. a relatively high birefringence film) even if it is quite out of line and the transmission level is lower. This is because use of the "line-shape" determination process, performed by the averaging module in the processor 504 (and discussed further later) puts a lot more weight to the flatness of the line than its average intensity. Thus, a colour measurement system as illustrated in FIG. 10 is able to interpret colour information in addition to intensity information to avoid the loss of information which may occur in a white-light single-detector integrating system. An authentication determination may be made by the processor 504 in this arrangement based upon both sets of information.

A counterfeiter aware of the limitations of systems which determine authenticity based upon measurements of birefringence under white-light conditions only may seek to create a counterfeit security document in which the machine and transverse directions of a relatively high birefringence non-genuine polymer film substrate are skewed relative to the edges of the substrate. That is, the machine and transverse directions of the substrate may be non-parallel to edges of the substrate. Thus, when a counterfeit security document of this type is introduced into a system which determines authenticity based upon measurements of birefringence using white-light emitter, single integrating detector techniques, the counterfeit security document, to the naked eye, may appear to be properly aligned. In fact, however, the machine and transverse directions of the substrate will be misaligned relative to the apparatus and may mimic the effect which would be observed if a film substrate of lower birefringence was present. That is, the misalignment causes an observation of a lower birefringence than would otherwise have been observed if the non-genuine, higher birefringence, film had been configured so that the machine and transverse directions were aligned.

The apparatus described above in relation to FIG. 10 may be suitable for the detection of counterfeit security documents formed on non-bubble process film substrates (i.e. those film substrates having a relatively high birefringence e.g. stenter films) where the machine direction and transverse direction of the polymer film substrate are deliberately arranged so as to be misaligned when placed in the apparatus.

The authentication apparatus 500 illustrated in FIG. 10 differs from some of those previously described in that there is a single fixed detector 514 and in that it further comprises at least one wavelength filtering element 518.

The at least one wavelength filtering element 518 is operative to be located in a beam path of electromagnetic radiation travelling between emitter 510 and detector 516.

In the illustrated arrangement, the wavelength filtering element 518 is operative to transmit a portion of wavelengths of the polarised transmitted electromagnetic radiation before being received by the detector 516. In optional arrangements where a plurality of wavelength filtering elements 518 are provided, each of said plurality of wavelength filtering elements 518 may serve to transmit different portions (i.e. different wavelength ranges) of the spectrum of polarised transmitted electromagnetic radiation. Placement of one of the plurality of wavelength filtering elements 518 in the beam path may be effected by an actuator (not shown) controlled by the processor 504. In this optional arrangement, the apparatus is operative to select different portions of the spectrum of the polarised transmitted electromagnetic radiation upon which to perform a detection measurement at the detector 516.

In operation therefore, transmitted electromagnetic radiation TL transmitted by said item 508 is polarised by second polariser 514 as it passes therethrough, and a portion of the transmitted electromagnetic radiation TL transmitted by said item 508 continues as polarised transmitted electromagnetic radiation (denoted by arrow PTL) towards detector 516. Before reaching detector 516, the polarised transmitted electromagnetic radiation PTL is incident upon wavelength filtering element 518. Certain wavelengths of the incident polarised transmitted electromagnetic radiation PTL are not transmitted (e.g. reflected or absorbed) and a remaining portion of wavelengths are transmitted by the wavelength filtering element 518. This remaining portion (hereinafter "filtered transmitted radiation" FTL) continues to the detector 516 and is received thereat.

The detector 516, responsive to detection of filtered transmitted radiation FTL incident thereon, outputs a signal proportional to the intensity of filtered transmitted radiation FTL to the processor 504.

The processor 504 is operative to implement a process for converting a spectrum into a single value. The process is described in more detail below. This single value is based on an average value plus a factor that describes how flat the spectrum is. A flat spectrum will return a value approximately equal to the average value of the spectrum (or the integrated intensity): bubble films will fall into this category. As birefringence increases, the spectrum becomes tilted and eventually much more complex, so the variance value portion increases to become dominant—therefore highly birefringent materials will score values that are much greater. A white-light single-detector integrating system of the type described above employing the 0 to 1 standardised measurement scale will give a reading of "0" when empty and "1" (when a "half-wave" film is located in the system). This corresponds roughly to the scale on the graph of FIG. 11.

In order to calibrate the authentication apparatus 500, an operator may perform a calibration process prior to commencing an authentication process.

A "dark" reading may be taken, i.e. a spectrum of the empty measurement region of the apparatus with the emitter 510 off. A "light" reading is also taken, i.e. a spectrum of the empty measurement region with the emitter 510 on. The processor 504 is operative to flag the measurement values obtained from these readings with representations indicating that they are "dark" and "light" readings. The processor 504 is further operative to communicate the measurement values to suitable storage means for retrieval at some other point in time.

Once the calibration process is complete, the authentication apparatus 500 is then ready to authenticate samples.

When a sample item/film 508 is located in the measuring region of the authentication apparatus 500, a sample reading is taken, i.e. a spectrum of the measurement region with the sample located therein and the lights on.

The range of measurement values output by the detector 516 to the processor 504 is operated upon by the processor to calculate a result spectrum. The processor 504 is operative to implement the following calculation to calculate the result spectrum:

resultSpectrum=(sampleReading−darkReading)/
(lightReading−darkReading)

The processor 504 is operative to "smooth" the calculated result spectrum using an averaging module (not shown). The process effected by the averaging module is as follows:

temp[$j$]=(resultSpectrum[$j$−3]+resultSpectrum[$j$−2]+
resultSpectrum[$j$−1]+resultSpectrum[$j$]+resultSpectrum[$j$+1]+resultSpectrum[$j$+2]+resultSpectrum[$j$+3])/7

This "smoothing" function may reduce the effect of random noise on the sample's variance.

Each result (temp[j]) is averaged with +/−3 results on either side of the result throughout the spectrum.

The processor 504 is operative, using the averaging module, to then calculate an average value of the spectrum, and a statistical variance of the spectrum.

The processor 504 is then operative, using the averaging module, to calculate a polynomial of a first-order (i.e. black to white) retarding spectrum from a theoretical ideal shape using the average of the real spectrum to position its intensity.

The processor 504 is then operative, using the averaging module, to calculate the variance of this result spectrum from the general shape of the polynomial.

The processor 504 is operative to make a decision that if the variance is above a certain level, a polynomial correction is applied. The reason for this is, for low levels of birefringence, the calculated spectrum line tilts towards the red end of the spectrum. Correcting this flattens low birefringence lines, thereby reducing the effect of this tilt upon the variance. However, if this tilt is applied to birefringence results close to the end of the first order (see Michel-Levy chart) it can either reduce the final variance or unfairly increase the variance of borderline films.

The processor 504 re-calculates the variance of the flattened line if it determines that the polynomial correction has been applied.

The calculated variance describes the flatness of the line (as noted above). The flatter the line, the lower the variance. As all low birefringence lines have been flattened according to the theoretical polynomial, birefringence of the first order will be equivalent to the average intensity. The formula is used to describe the line:

Result=average+100*variance

Using this technique, the result is very sensitive to variations in line flatness, the following results are obtained:
- 0-0.8=agrees closely with the current white-light single-detector integrating system 0 to 1 (half-wave plate) scale.
- 0.8-1.2=as the line begins to tilt, there is a loss in accuracy in this region which roughly corresponds to 0.8-1 on the white-light single-detector integrating system 0 to 1 scale.
- 1.2-30—as the line becomes coloured, the variance increases dramatically. Stenter films score at least 9 and often much higher. This is equivalent to 0.5-1 on the 0 to 1 scale: a situation brought about by the white-light single-detector integrating system.

The processor, after implementing the above-described process, is operative to compare values (or a spectrum) calculated using said process (which are representative of the received signal) with a set of pre-defined values (or a pre-defined spectrum) stored in a database (not shown). These pre-defined values (or pre-defined spectrum) correspond to expected filtered transmitted radiation FTL values (when a particular wavelength filtering element 518 is employed), or a pre-defined spectrum, when an authentic item (e.g. an authentic film) is located in the measuring region.

The processor 504, after conducting the comparison, is operative to instruct the alert system 506 to indicate that the film/item is authentic or non-authentic. If the result of the comparison is positive (i.e. the film is authentic), the processor is operative to send a signal to the alert system 506 containing an instruction to issue an indication that the film/item is authentic. Otherwise, the processor is operative to send a signal to the alert system 506 containing an instruction to issue an indication that the film/item is non-authentic.

In an optional arrangement of the arrangement illustrated in FIGS. 7a and 7b, rather than a single second polariser rotatable between an orientation in which the polarising direction is crossed with respect to that of the first polariser and an orientation in which the polarising direction is the same as that of the first polariser, the second polariser may, in fact, comprise two separate second polarisers having different orientations which can be placed in the beam path depending on which type of transmission is required (i.e. crossed polarisation compared with the first polariser or parallel polarisation compared with the first polariser)

In an optional arrangement of the arrangement illustrated in FIG. 10, a white light emitter source may be used in conjunction with a spectrometer as the detector 516. In such an arrangement, wavelength filtering element 518 is not required.

In another optional arrangement of the arrangement illustrated in FIG. 10, the emitter 510 may comprise a white-light source and the detector 516 may comprise an array of photodiodes with a corresponding array of wavelength filtering elements 518 (optionally different coloured filters). For example, the apparatus 500 may comprise a white LED as the emitter 510, and three photodiodes operative as the detector 516. A first of the three photodiodes may have a corresponding blue filter as its associated wavelength filtering element 518, a second of the three photodiodes may have a corresponding green filter as its associated wavelength filtering element 518, and a third of the three photodiodes may have a corresponding red filter as its associated wavelength filtering element 518.

In another optional arrangement of the arrangement illustrated in FIG. 10, the emitter 510 may comprise an array of emitters, each operative to emit light of a different colour. The detector 516 may comprise an array of corresponding detectors, each one responsive to light of a particular colour emitted by an associated one of the array of emitters.

In another optional arrangement of the arrangement illustrated in FIG. 10, the emitter 510 may comprise an electromagnetic emitter source, or array of sources, controllable to emit white light, light of a particular colour, (i.e. light in a specific wavelength range of the visible electromagnetic spectrum), and/or light of a mixture of colours (but not all colours). This may be implemented using a white light LED of a type which comprises red, green and blue LEDs located in the white light LED housing. The red, green and blue LEDs can be illuminated together to produce white light. However, by adapting the white light LED so that each of the red, green and blue LEDs is individually controllable, white light, coloured light (e.g. red only, blue only or green only), or mixed colour light (e.g. red and green light, blue and green light, blue and red light) may be obtained by controlling which LEDs (or combinations of LEDs) are illuminated.

This optional arrangement of the arrangement illustrated in FIG. 10 may be suitable for determining if a film being tested is of a first type, or otherwise, or at least a second type or otherwise. A film of the first type may be, for example, a film formed using the bubble process. A film of the at least second type may be, for example, a film formed using the stenter process. The apparatus may be employed to identify genuine films of the first type, genuine films of the at least second type, and non-genuine films.

The arrangement will be described further with reference to FIGS. 13 to 16.

FIG. 13 schematically illustrates a perspective view of an optional arrangement of the apparatus illustrated in FIG. 10. In this optional arrangement, the emitter 510 comprises an electromagnetic emitter source controllable to emit white light (WL) or light of a particular colour (CL) depending on a mode of operation.

Different emitter sources will produce different intensity versus retardation curves. Thus, an intensity versus retardation curve where the emitter source emits white light will differ from an intensity versus retardation curve where the emitter source emits coloured light.

FIG. 14 illustrates a graph of retardation versus intensity as measured by the detector 516 of the apparatus 500 of FIG. 13 when the apparatus operates in a first mode such that the emitter 510 emits white light and the detector 516 receives white light (PTL). FIG. 15 illustrates a graph of retardation versus intensity as measured by the detector 516 of the apparatus 500 of FIG. 13 when the apparatus operates in a second mode such that the emitter 510 emits coloured light and the detector 516 receives coloured light (PTL). FIG. 16 illustrates a combined graph of the graphs of FIGS. 14 and 15.

An intensity curve illustrated in FIG. 14 corresponds to the intensity of electromagnetic radiation received by the detector 516 for different film types (i.e. different retardation values) when the emitter 510 operates in a first mode to emit white light. A polymer film manufactured using a bubble process will generally have a retardation value in the range 0 to 120 nm (denoted by box R in FIG. 14). As can be seen from the curve illustrated in FIG. 14, the intensity signal for a polymer film having a retardation value within this range will be relatively low compared to films having higher retardation values.

Therefore, the arrangement could be used to determine if a film under test is one which is manufactured using a bubble process (i.e. a film having a low retardation value) if the intensity value of white light electromagnetic radiation received by the detector is less than 0.2. Thus, in the first mode of operation, the apparatus 500 can categorise a film under test as a first type (i.e. as made using a bubble process) if the intensity value is less than 0.2, or at least a second, or some other, type if the intensity value is more than 0.2.

In some instances, it may be desirable to determine the authenticity of an item comprising a polymer substrate which has been formed by a non-bubble process (e.g. a stenter film). If the apparatus 500 is to be used in such a manner, then a first mode measurement and a second mode measurement must be used to make such an authenticity determination.

A fairly common polymer film manufactured using a stenter process will generally have a retardation value in the range 900 to 1100 nm (denoted by box $S_1$). Referring again to FIG. 14, it can be seen that a film with a retardation value in this range will produce a received intensity of white light at the detector 516 (when the apparatus is operating in the first mode) with a value of between 0.5 and 0.6. However, and as can be seen from the figure, an intensity value of 0.5 to 0.6 is fairly common throughout the spectrum at both higher and lower retardation values. In fact, such an intensity value may also occur where the film under test has a retardation between: about 1400 nm to about 1700 nm (denoted by box $S_2$); about 2100 nm to about 2400 nm (denoted by box $S_3$); about 2800 nm to about 3200 nm (denoted by box $S_4$); and about 3500 nm to about 3900 nm (denoted by box $S_5$).

As will be appreciated, therefore, using an intensity value of between 0.5 and 0.6 will not permit a retardation value for the film under test to be determined because received white light electromagnetic radiation at a value in this range corresponds to multiple possible film retardation values.

Although the intensity value range of 0.5 and 0.6 can be used to eliminate films which give rise to intensity values outside of this range, as mentioned above, a further step is required in order to determine if the film under test has a retardation value within the required range.

In summary of the process thus far, if the intensity value of the white light received by the detector 516 is less than 0.2 (i.e. a first mode first threshold value), then the apparatus 500 indicates that film under test is of a first type (i.e. a bubble process film). If the intensity value of the white light received by the detector 516 is between 0.5 and 0.6 (i.e. above the first threshold value but between a first mode second threshold value and a first mode third threshold value), the apparatus 500 must proceed to a second mode of operation (described further below) in order to make a determination of the retardation value (and thus of whether or not the film is of a second type). If the intensity value of white light received by the detector 516 is both greater than the first mode first threshold value (i.e. 0.2) and outside the range of values between the first mode second threshold value (i.e. 0.5) and the first mode third threshold value (i.e. 0.6), then the apparatus 500 is operative to indicate that the film under test is of a non-genuine type.

The second mode of operation will be described in relation to FIG. 15, In this mode of operation, the emitter 510 operates to emit coloured light using two sources (a source which emits light at 490 nm and a source which emits light at 540 nm). Of course, in other arrangements, different sources operative to emit light at different wavelengths may be used.

Thus, the intensity curve in FIG. 15 corresponds to the coloured light received at the detector 516 using the above sources as the emitter 510. Again, the polymer film manufactured using the bubble process and having a retardation value in the range 0 to 120 nm is denoted by box R in this figure.

The polymer film manufactured using a stenter process and having a retardation value in the range 900 to 1100 nm (denoted by box $T_1$ in this figure) will produce an intensity value at the detector 516 of about 0.1 to 0.2. As can be seen from FIG. 15, there are two other film retardation value ranges which would produce roughly equivalent intensity values of 0.1 to 0.2 at the detector 516. These are: a retardation value in the range 50 to 120 nm (i.e. within box R corresponding to the bubble process film); and a retardation value in the range about 450 nm to about 600 nm (denoted by box $T_2$ in this figure). However, the retardation values in the range within box R and within box $T_2$ can be eliminated by the processor 504 when the intensity value measurement from the first mode of operation is also considered. These processing steps can be seen by overlying the intensity curve of FIG. 14 with that of FIG. 15 as illustrated in FIG. 16.

In FIG. 16, the box $S_1$ & $T_1$ denotes the combination of the parameters from the both first mode of operation and the second mode of operation. That is, if the film under test gives rise to intensity values which satisfy the boundary parameters in both the first and second modes of operation, the apparatus determines that the film under test is of a second type, i.e. in this instance, a genuine stenter film.

Thus, if, in the first mode of operation the intensity value of the white light received by the detector 516 is between 0.5 and 0.6 (i.e. above the first threshold value but between a first mode second threshold value and a first mode third threshold value), the apparatus 500 proceeds to implement a second mode of operation. If, in the second mode of operation, the intensity value of coloured light received by the detector 516 is between about 0.1 (a second mode first threshold value) and about 0.2 (a second mode second threshold value) the apparatus is operative to determine that the film under test is of a second genuine type (e.g. a genuine stenter film). However, if after implementing the second mode of operation, the intensity value of coloured light received by the detector 516 is outside the range of values between the second mode first threshold value (i.e. 0.1) and the second mode second threshold value (i.e. 0.2), then the apparatus 500 is operative to indicate that the film under test is of a non-genuine type.

The above-described algorithm implemented by the processor 504 may be summarised as follows:

Mode 1 (White Light)
 a) If the intensity value at the detector is less than about 0.2, the apparatus is operative to provide an indication that the film is genuine and of a first type; or
 b) If the intensity value at the detector is between about 0.5 and about 0.6, the apparatus is operative to implement mode 2; or
 c) If the intensity value at the detector is greater than about 0.2 and not between about 0.5 and 0.6, the apparatus is operative to provide an indication that the film is non-genuine.

Mode 2 (Coloured Light)
 a) If the intensity value at the detector is between about 0.1 and about 0.2, the apparatus is operative to provide an indication that the film is genuine and of a second type; or
 b) If the intensity value at the detector is not between about 0.1 and about 0.2, the apparatus is operative to provide an indication that the film is non-genuine.

It should be appreciated that the apparatus 500 could be configured to detect for other genuine films types simply by altering the threshold values in the first and/or second modes of operation. That is, the technique employed by the apparatus 500 could be used to determine authenticity of films having any range of retardation values.

Further, the apparatus 500 could be configured to illuminate a sample film under test with different colour light source combinations. Thus, instead of a white light source in the first mode and a coloured light source in the second mode, the apparatus may employ a first coloured light source in the first mode and a second coloured light source in the second mode. Optionally, there may be greater than two modes of operation, e.g. a first coloured light source operable in a first mode, a second coloured light source operable in a second mode, a third coloured light source in a third mode, and so on.

In one or more of the above-described embodiments, the authentication apparatus may further comprise a data storage element (e.g. ROM) for storing predetermined birefringence characteristic data and other optical characteristic data, and a working memory or cache (e.g. RAM).

In yet further optional arrangements, one or more of the features of the above-described one or more embodiments (as illustrated in FIGS. 4a to 4b, 5, 6, 7, 8, 9, 10 and 13) may be employed in different combinations to form other embodiments of the authentication apparatus.

In the illustrated one or more embodiments, point electromagnetic radiation emission sources and point detectors are shown. However, in optional arrangements, linear electromagnetic radiation emission sources and/or linear detectors may be used. In yet further optional arrangements, a combination of point sources, linear sources, point detector and/or linear detectors may be used.

In the description above, any reference to "light" is intended to include electromagnetic radiation in both the "visible" part of the electromagnetic spectrum and also the "invisible" part of the electromagnetic spectrum. Further, any reference to the "visible" part of the electromagnetic spectrum is intended to include infra-red and ultra-violet light.

Insofar as embodiments of the invention described above are implementable, at least in part, using a software-controlled programmable processing device such as a general purpose processor or special-purposes processor, digital signal processor, microprocessor, or other processing device, data processing apparatus or computer system it will be appreciated that a computer program for configuring a programmable device, apparatus or system to implement methods and apparatus is envisaged as an aspect of the present invention. The computer program may be embodied as any suitable type of code, such as source code, object code, compiled code, interpreted code, executable code, static code, dynamic code, and the like. The instructions may be implemented using any suitable high-level, low-level, object-oriented, visual, compiled and/or interpreted programming language, such as, Liberate, OCAP, MHP, Flash, HTML and associated languages, JavaScript, PHP, C, C++, Java, BASIC, Perl, Matlab, Pascal, Visual BASIC, JAVA, ActiveX, assembly language, machine code, and so forth. A skilled person would readily understand that term "computer" in its most general sense encompasses programmable devices such as referred to above, and data processing apparatus and computer systems.

Suitably, the computer program is stored on a carrier medium in machine readable form, for example the carrier medium may comprise memory, removable or non-removable media, erasable or non-erasable media, writeable or re-writeable media, digital or analog media, hard disk, floppy disk, Compact Disk Read Only Memory (CD-ROM), Company Disk Recordable (CD-R), Compact Disk Rewriteable (CD-RW), optical disk, magnetic media, magneto-optical media, removable memory cards or disks, various types of Digital Versatile Disk (DVD) subscriber identity module, tape, cassette solid-state memory.

As used herein any reference to "one embodiment" or "an embodiment" means that a particular element, feature, structure, or characteristic described in connection with the embodiment is included in at least one embodiment. The appearances of the phrase "in one embodiment" in various places in the specification are not necessarily all referring to the same embodiment.

As used herein, the terms "comprises," "comprising," "includes," "including," "has," "having" or any other variation thereof, are intended to cover a non-exclusive inclusion. For example, a process, method, article, or apparatus that comprises a list of elements is not necessarily limited to only those elements but may include other elements not expressly listed or inherent to such process, method, article, or apparatus. Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

In addition, use of the "a" or "an" are employed to describe elements and components of the invention. This is done merely for convenience and to give a general sense of the invention. This description should be read to include one or at least one and the singular also includes the plural unless it is obvious that it is meant otherwise.

In view of the foregoing description it will be evident to a person skilled in the art that various modifications may be made within the scope of the invention.

The scope of the present disclosure includes any novel feature or combination of features disclosed therein either explicitly or implicitly or any generalisation thereof irrespective of whether or not it relates to the claimed invention or mitigate against any or all of the problems addressed by the present invention. The applicant hereby gives notice that new claims may be formulated to such features during prosecution of this application or of any such further application derived therefrom. In particular, with reference to the appended claims, features from dependent claims may be combined with those of the independent claims and features from respective independent claims may be combined in any appropriate manner and not merely in specific combinations enumerated in the claims.

The invention claimed is:

1. An authentication apparatus operative to determine the authenticity of a polymer film, comprising an optically-based birefringence measuring arrangement operative to measure a first effect influenced by a birefringence characteristic of said film from a first angle comprising a non-normal angle to a plane of said film, and at least one of: a second angle; and a third angle; and wherein said apparatus is operative to:
    compare a value, or range of values, representative of said first effect as measured from said first angle with a value, or range of values representative of a specified first effect corresponding to a predetermined birefringence characteristic of an authentic polymer film for said first angle;
    compare a value, or range of values, representative of said first effect as measured from said at least one of said second and third angles with a value, or range of values representative of a specified first effect corresponding to a predetermined birefringence characteristic of an authentic polymer film for respective second and/or third angles; and
    output an authenticity signal indicative of authenticity or otherwise of said film based upon said comparisons,
    wherein said optically-based birefringence measuring arrangement comprises:
        an emitter located, and operative, to illuminate said film with electromagnetic radiation;
        a first polariser located between said emitter and a first side of said film so that at least a portion of electromagnetic radiation emitted by said emitter passes therethrough;
        a first detector located on a second side of said film, and operative to receive electromagnetic radiation from said emitter transmitted through said film and communicate said authenticity signal to a processor; and
        a second polariser located between a second side of said film and said detector so that at least a portion of electromagnetic radiation transmitted through said film passes therethrough,
    wherein said processor is operative to compare said values and output the authenticity signal indicative of authenticity or otherwise of said film based upon said comparisons.

2. The apparatus according to claim 1, wherein said second angle comprises a non-normal angle to a plane of said film and said third angle comprises a normal angle to a plane of said film.

3. The apparatus according to claim 1, wherein said apparatus is operative to differentiate between films made by a bubble process and films made by a different process.

4. The apparatus according to claim 1, wherein said optically-based birefringence measuring arrangement comprises an emitter located, and operative, to illuminate a first side of said film located in a measuring region of said apparatus with electromagnetic radiation; a first polariser located between said first emitter and said first side of said film so that at least a portion of electromagnetic radiation emitted by said first emitter passes therethrough; a first detector located on a second side of said film, and operative to receive electromagnetic radiation from said emitter transmitted through said film and transmitted from said second side of said film at said first angle and at least one of said second and third angles; a second polariser located between said second side of said film and said first detector so that at least a portion of electromagnetic radiation transmitted through said film passes therethrough, wherein said first detector is operative to output a signal representative of said first effect as measured based upon electromagnetic radiation transmitted from said second side of said film at said first angle and at least one of said second and third angles.

5. The apparatus according to claim 4, wherein said first detector is movable relative to said second side of said film for location at a first position to receive electromagnetic radiation from said emitter transmitted through said film and transmitted from said second side of said film at said first angle, and further movable to a second and/or third position to receive electromagnetic radiation from said emitter transmitted through said film and transmitted from said second side of said film at respective said second and/or third angles.

6. The apparatus according to claim 4 further comprising:
    a second detector located on a second side of said film, and operative to receive electromagnetic radiation from said emitter transmitted through said film and transmitted from said second side of said film at said second angle; and/or
    a third detector located on a second side of said film, and operative to receive electromagnetic radiation from said emitter transmitted through said film and transmitted from said second side of said film at said third angle;

wherein:

said second detector is operative to output a signal representative of said first effect as measured based upon electromagnetic radiation transmitted from said second side of said film at said second angle; and/or said third detector is operative to output a signal representative of said first effect as measured based upon electromagnetic radiation transmitted from said second side of said film at said third angle.

7. The apparatus according to claim 1, wherein said first angle comprises one of:

(i) that described by vector [101] with respect to the film; and (ii) that described by vector [111] with respect to the film.

8. The apparatus according to claim 7, wherein said second angle comprises the other of:

(i) that described by vector [101] with respect to the film; and (ii) that described by vector [111] with respect to the film.

9. The apparatus according to claim 4, wherein an output signal outputted by said first detector is proportional to an intensity of transmitted electromagnetic radiation received.

10. The apparatus according to claim 9, wherein said first detector is operative to communicate said output signal to a processor which is operative to compare a value of said output signal representative of said first effect as measured from said first angle with said value or range of values representative of a specified first effect corresponding to a predetermined birefringence characteristic of an authentic polymer film for said first angle.

11. The apparatus according to claim 10, wherein said value or range of values comprises at least one expected first detector output signal value representative of electromagnetic radiation transmitted from said second side of said film at said first angle and received by said first detector if an authentic film is located in said measuring region.

12. The apparatus according to claim 6, wherein an output signal output by said second detector and/or said third detector is proportional to an intensity of transmitted electromagnetic radiation received.

13. The apparatus according to claim 12, wherein:

said second detector is operative to communicate said output signal to a processor which is operative to compare a value of said output signal representative of said first effect as measured from said second angle with said value or range of values representative of a specified first effect corresponding to a respective predetermined birefringence characteristic of an authentic polymer film for said second angle; and/or said third detector is operative to communicate said output signal to a processor which is operative to compare a value of said output signal representative of said first effect as measured from said third angle with said value or range of values representative of a specified first effect corresponding to a respective predetermined birefringence characteristic of an authentic polymer film for said third angle.

14. The apparatus according to claim 13, wherein:

said value or range of values comprises at least one expected second detector output signal value representative of electromagnetic radiation transmitted from said second side of said film and received by said second detector if an authentic film is located in said measuring region; and/or said value or range of values comprises at least one expected third detector output signal value representative of electromagnetic radiation transmitted from said second side of said film and received by said third detector if an authentic film is located in said measuring region.

15. A method of determining the authenticity of a polymer film with an authentication apparatus comprising an optically-based birefringence measuring arrangement comprising an emitter located, and operative, to illuminate said film with electromagnetic radiation; a first polariser located between said emitter and a first side of said film so that at least a portion of electromagnetic radiation emitted by said emitter passes therethrough; a detector located on a second side of said film, and operative to receive electromagnetic radiation from said emitter transmitted through said film and communicate said authenticity signal to a processor; and a second polariser located between a second side of said film and said detector so that at least a portion of electromagnetic radiation transmitted through said film passes therethrough, wherein said processor is operative to compare said values and output the authenticity signal indicative of authenticity or otherwise of said film based upon said comparisons, said method comprising:

illuminating said film with electromagnetic radiation from said emitter;

detecting electromagnetic radiation transmitted through said film from said emitter by said detector and communicated to said processor, measuring a first effect influenced by a birefringence characteristic of said film from a first angle comprising a non-normal angle to a plane of said film, and at least one of: a second angle; and a third angle;

comparing a value, or range of values, representative of said first effect as measured from said first angle with a value, or range of values representative of a specified first effect corresponding to a predetermined birefringence characteristic of an authentic polymer film for said first angle;

comparing a value, or range of values, representative of said first effect as measured from said at least one of said second and third angles with a value, or range of values representative of a specified first effect corresponding to a predetermined birefringence characteristic of an authentic polymer film for respective second and/or third angles; and outputting an authenticity signal indicative of authenticity or otherwise of said film based upon said comparisons.

* * * * *